(12) United States Patent
Rosenblatt et al.

(10) Patent No.: US 10,744,232 B2
(45) Date of Patent: Aug. 18, 2020

(54) ANTIMICROBIAL CATHETERS

(71) Applicant: Board of Regents, The University of Texas System, Austin, TX (US)

(72) Inventors: Joel Rosenblatt, Pottstown, PA (US); Issam Raad, Missouri City, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 14/784,747

(22) PCT Filed: Apr. 17, 2014

(86) PCT No.: PCT/US2014/034551
§ 371 (c)(1),
(2) Date: Oct. 15, 2015

(87) PCT Pub. No.: WO2014/172569
PCT Pub. Date: Oct. 23, 2014

(65) Prior Publication Data
US 2016/0074560 A1    Mar. 17, 2016

Related U.S. Application Data

(60) Provisional application No. 61/813,542, filed on Apr. 18, 2013.

(51) Int. Cl.
*A61L 29/08* (2006.01)
*A61L 29/16* (2006.01)
(Continued)

(52) U.S. Cl.
CPC .............. *A61L 29/16* (2013.01); *A61K 31/14* (2013.01); *A61K 31/155* (2013.01);
(Continued)

(58) Field of Classification Search
CPC ......... A61M 2025/0056; A61K 31/155; A61K 31/165; A61K 45/06; A61L 29/16;
(Continued)

(56) References Cited

U.S. PATENT DOCUMENTS 4,925,668 A    5/1990    Khan et al.
5,019,096 A    5/1991    Fox, Jr. et al.
(Continued)

FOREIGN PATENT DOCUMENTS

EP    0214721    3/1987
EP    2 314 324    4/2011
(Continued)

OTHER PUBLICATIONS

Extended European Search Report dated European Application No. 14785648.8, dated Nov. 11, 2016.
(Continued)

*Primary Examiner* — Dinah Baria
(74) *Attorney, Agent, or Firm* — Parker Highlander PLLC

(57) ABSTRACT

Antimicrobial catheters and medical devices are provided. In some aspects, a low durometer aliphatic polyether polyurethane may be impregnated with a first antimicrobial agent (e.g., minocycline and rifampin) and coated with a second antimicrobial agent (e.g., chlorhexidine, gendine, or gardine). The antimicrobial catheters may display improved flexibility and resistance to kinking. Methods of producing the antimicrobial catheters are also provided.

32 Claims, 10 Drawing Sheets

(51) Int. Cl.
*A61L 29/06* (2006.01)
*A61K 45/06* (2006.01)
*A61K 31/155* (2006.01)
*A61K 31/496* (2006.01)
*A61K 31/14* (2006.01)
*A61K 31/65* (2006.01)
*A61K 31/165* (2006.01)
*A61M 25/00* (2006.01)

(52) U.S. Cl.
CPC .......... *A61K 31/165* (2013.01); *A61K 31/496* (2013.01); *A61K 31/65* (2013.01); *A61K 45/06* (2013.01); *A61L 29/06* (2013.01); *A61L 29/08* (2013.01); *A61L 29/085* (2013.01); *A61L 2300/206* (2013.01); *A61L 2300/404* (2013.01); *A61L 2300/406* (2013.01); *A61L 2300/442* (2013.01); *A61L 2300/606* (2013.01); *A61L 2420/02* (2013.01); *A61L 2420/06* (2013.01); *A61L 2420/08* (2013.01); *A61M 25/0009* (2013.01); *A61M 2025/0056* (2013.01); *A61M 2025/0057* (2013.01)

(58) Field of Classification Search
CPC ............... A61L 29/08; A61L 2300/606; A61L 2300/206; A61L 2300/404; A61L 2300/406; A61L 2300/442
See application file for complete search history.

(56) References Cited

U.S. PATENT DOCUMENTS

| | | | |
|---|---|---|---|
| 5,165,952 A * | 11/1992 | Solomon | A61L 29/06 424/78.08 |
| 5,217,493 A | 6/1993 | Raad et al. | |
| 5,453,099 A | 9/1995 | Lee et al. | |
| 5,458,935 A | 10/1995 | Alzner | |
| 5,624,704 A | 4/1997 | Darouiche et al. | |
| 5,688,516 A * | 11/1997 | Raad | A61L 29/08 424/405 |
| 5,902,283 A | 5/1999 | Darouiche et al. | |
| 6,582,719 B2 | 6/2003 | Modak et al. | |
| 7,651,661 B2 | 1/2010 | Raad et al. | |
| 7,713,472 B2 | 5/2010 | Raad et al. | |
| 2001/0010016 A1 * | 7/2001 | Modak | A01N 59/16 623/1.42 |
| 2003/0078242 A1 | 4/2003 | Raad et al. | |
| 2003/0157193 A1 * | 8/2003 | McDonald | A01N 25/10 424/667 |
| 2006/0009099 A1 * | 1/2006 | Jonn | A61L 15/58 442/43 |
| 2007/0129690 A1 * | 6/2007 | Rosenblatt | A61L 29/16 604/265 |
| 2007/0154621 A1 | 7/2007 | Raad | |
| 2010/0069854 A1 * | 3/2010 | Okoh | A61L 27/54 604/265 |
| 2011/0071478 A1 | 3/2011 | Liu et al. | |
| 2012/0064372 A1 * | 3/2012 | Raad | A61L 27/54 428/704 |

FOREIGN PATENT DOCUMENTS

| | | |
|---|---|---|
| JP | 2012-045038 | 3/2012 |
| WO | WO 1996/022114 | 7/1996 |
| WO | WO 1996/023602 | 8/1996 |
| WO | WO 2010-104760 | 9/2010 |
| WO | WO 2013/013172 | 1/2013 |
| WO | WO 2013-070951 | 5/2013 |

OTHER PUBLICATIONS

Hachem et al., "Novel antiseptic urinary catheters for prevention of urinary tract infections: correlation of in vivo and in vitro test results," *Antimicrob. Agents Chemother*, 53(12):5145-5149, 2009.
Hanna et al. "Comparative in vitro efficacies and antimicrobial durabilities of novel antimicrobial central venous catheters," *Antimicrob. Agents Chemother*, 50(10): 3283-3288, 2006.
Hébert et al., "Persistent Inhibition of Platelets During Continuous Nitroglycerin Therapy Despite Hemodynamic Tolerance," *Circulation*, 95(5):1308-1313, 1997.
Lacoste et al., "Antithrombotic properties of transdermal nitroglycerin in stable angina pectoris," *The American Journal of Cardiology*, 73(15):1058-1062, 1994.
PCT International Search Report and Written Opinion issued in International Application No. PCT/US2014/034551, dated Nov. 24, 2014.
Raad et al., "Central venous catheters coated with minocycline and rifampin for the prevention of catheter-related colonization and bloodstream infections. A randomized, double-blind trial. The Texas medical center catheter study group." *Ann Intern Med.*, 127(4):267-274, 1997.
Raad et al., "The broad-spectrum activity and efficacy of catheters coated with minocycline and rifampin," *The Journal of Infectious Diseases*, 173:418-424, 1996.
Raaz et al., "The direct thrombin inhibitor argatroban effectively prevents cardiac catheter thrombosis in vitro," *Thromb Haemost.*, 103(4):808-814, 2010.
Office Action issued in Japanese Application No. 2016-509106, dated Dec. 13, 2017, and English language translation thereof.
Chlorhexidine, PubChem CID 9552079, first page only, located at https://pubchem.ncbi.nlm.nih.gov/compound/chlorhexidine, accessed Mar. 27, 2019.
Office Action issued in European Application No. 14785648.8, dated Mar. 15, 2019.
Response submitted in European Application No. 14785648.8, filed Oct. 24, 2018.
Office Action issued in Japanese Application No. 2016-509106, dated Nov. 8, 2018, and English language translation thereof.

* cited by examiner

ANTIMICROBIAL CATHETERS

This application is a national phase application under 35 U.S.C. § 371 of International Application No. PCT/US2014/034551, filed Apr. 17, 2014, which claims the benefit of U.S. Provisional Patent Application No. 61/813,542, filed Apr. 18, 2013, the entirety of each of which is incorporated herein by reference.

BACKGROUND OF THE INVENTION

1. Field of the Invention

The present invention relates generally to the field of medical devices and medicine. More particularly, it concerns antimicrobial catheters with improved antimicrobial and physical properties.

2. Description of Related Art

Vascular catheters are important life saving devices with widespread use. They provide direct, immediate access to the bloodstream for a variety of critical purposes including transfusions, administering medications, nutrition, blood sampling for testing, and cardiac pressure and output monitoring. Catheters with multiple lumens are often used to meet these different needs.

Although catheters can provide many benefits, a significant risk of infection remains. Because vascular catheters provide access across surfaces that are ordinarily sealed from external environments, they can serve as conduits for pathogenic micro-organisms to colonize catheter surfaces and gain access to the bloodstream. Potential complications include bacteremia and bloodstream infection. Catheter associated blood stream infections can be costly to treat and may also result in significant adverse effects including mortality. Antimicrobial catheters incorporate antimicrobial agents to prevent infections. The clinical benefits of specific antimicrobial catheters have been shown, and Minocycline/Rifampin and Chlorhexidine/Silver Sulfadiazine catheters have recently been accorded the highest level recommendation for use by the Center for Disease Control (CDC) committee on Central Line Associated Blood Stream Infections (CLABSIs). The organisms causing CLABSIs are consistently shifting in prevalence. Over the last decade the reported relative incidence of infection by Candidemia, Enterococcal, and gram negative organisms has increased. Accordingly, improved antimicrobial agent combinations are needed to respond to these new threats. Chlorhexidine has been combined with Minocycline and Rifampin (CH/M/R) to give broader spectrum protection. In other instances, the combination of chlorhexidine with triarylmethane dyes such as Gentian Violet (gendine) or Brilliant Green (gardine) have been used to provide improved antimicrobial protection.

The improvements in antimicrobial protection associated with CH/M/R and Gendine/Gardine combinations have lead to some undesirable complications or costs. As shown herein, one such complication is that the processes needed to incorporate these agents into vascular catheters can result in catheters that can display undesirable mechanical properties. Stiff catheters are generally required to withstand the solvents and penetrating agents required for impregnation of the antimicrobial agents. Residual stiffness in the catheters can irritate and inflame the blood vessels they reside within. This irritation is frequently a result of mechanical stress exerted by the catheter on the vessel wall. If the catheter is present in a vein, this can lead to phlebitis, stenosis, and/or thrombus formation. Other mechanical complications may also be associated with the function of catheters. In curved vessels, the bending of stiff or inelastic catheters can kink, causing lumens to seal under aspiration or have reduced cross-sectional area. As further shown herein, the introduction of several antimicrobial agents in combination can also create physical and chemical stability challenges associated with long-term storage. Antimicrobial agents may migrate over time to surfaces creating roughness or rapid release of the antimicrobial agents. Thrombus can also form on the catheter due to thrombin or platelet activation, which can occlude lumens. Methods involved with impregnating additional antimicrobial agents can raise the costs associated with making and packaging antimicrobial catheters to economically unattractive levels. Clearly, there remains a need for antimicrobial catheters with improved physical properties.

SUMMARY OF THE INVENTION

The present invention overcomes limitations in the prior art by providing in some aspects antimicrobial catheters with improved strength, stability, and/or flexibility. These improved physical properties may be observed over long-term storage of the catheters. Improved methods for producing low durometer antimicrobial polyether polyurethanes comprising antimicrobial agents are also provided. Teflon catheters, canulas, and tubing can be used in a variety of a medical applications including, e.g., subdermal infusion of medications from pumps such as insulin. To minimize infection risks associated with continuous infusion, manufacturers typically recommend rotating insertion sites every 1-3 days. Antimicrobial coatings and catheters as described herein may further reduce infection risk and/or increase the time between rotations of catheter placement, thereby reducing the costs and inconvenience associated with catheter exchanges.

An aspect of the present invention relates to a medical device comprising an aliphatic polyether polyurethane polymer having a durometer of A or B wherein the polyurethane is impregnated with minocycline and rifampin. The aliphatic polyether polyurethane polymer may have a durometer of A. The polyurethane may be coated or impregnated with a guanidium compound such as, e.g., chlorhexidine. The coating may further comprise a dye (e.g., gendine or gardine). The coating may comprise gendine, gardine, or chlorhexidine. The coating may comprise gendine, gardine, and chlorhexidine. The polyurethane may be coated with gendine, gardine, and chlorhexidine. The guanidium compound may be chlorhexidine. The medical device may further comprises a dye (e.g., gendine or gardine) impregnated into the polyurethane. In some embodiments, the polyurethane is impregnated with gendine, gardine, or chlorhexidine. In some embodiments, the polyurethane is impregnated with gendine, gardine, and chlorhexidine. The coating may comprise or be impregnated with a lower alcohol. In some embodiments, the polyurethane is impregnated with or coated with a fatty acid. The fatty acid may be caprylic acid (octanoic acid), caproic acid, lauric acid, or decanoic acid, hexanoic acid, or dodecanoic acid. The aliphatic polyether polyurethane polymer may have or comprise a repeating unit of the formula: $[O(CH_2)_n]_m$—$OC(O)NH$—$(CH_2)_x$—$NHC(O)$—; wherein n=1-4, x=1-12, and m is 1-100, wherein the repeating unit repeats 1-250 times, and the terminus of the polymer is hydrogen. In some embodiments, the repeating unit is repeated is 1-100, 2-100, 2-50, or 2-10 times. Larger repeating units may be used in some embodiments; for example, in some embodiments the repeating unit is repeated 100-500 or 100-1000 times. In some embodiments, m=1-50. In some embodiments, the repeating unit is repeated 1-100 times. In some embodiments, x=1-10. The polymer may further comprise a polymer coating comprising chlorhexidine, gendine, or gardine. The polymer coating may further comprise a polyurethane, a silicone, a vinyl, a fluoropolymer, an olefin, or a polymer blend or copolymer thereof. In some embodiments, the polymer coating is a polyurethane coating. The polyurethane coating may be an aliphatic polyether polyurethane. The polyurethane coating may have a durometer of A or D, or the coating may comprise a blend of A and D durometer aliphatic polyether polyurethanes. In some embodiments, the aliphatic polyether polyurethane is comprised in a coating on the medical device. In some embodiments, wherein the aliphatic polyether polyurethane is not comprised in a coating on the medical device. In some embodiments, the medical device does not comprise a penetrating or alkalizing agent. In some embodiments, the coating may be prepared with a blend of aliphatic polyurethane and hydrogel polyetherurethanes (e.g., Tecophilic®). For example, coatings may be prepared with blend ratios of about 0:100, 1:99, 10:90, 25:75, 50:50, 75:25, 90:10 or 100:0, or any range derivable therein, and total polyurethane concentrations may range, e.g., from about 5 to 11%. As shown in the below examples, blended coatings with 10% or more hydrogel polyetherurethane may display improved lubricity. In some embodiments, the coating may comprise Tecoflex® 60D and Tecoflex® 93A, optionally comprising an antimicrobial agent (e.g., chlorhexidine, etc.).

The medical device may be a catheter, an endotracheal tube, a nephrostomy tube, a biliary stent, an orthopedic device, a valve, a prosthetic valve, a drainage tube, a drain, a shunt, a staple, a clip, a mesh, a film, a blood exchanging device, a port, a cardiovascular device, a defibrillator, a pacemaker lead, a wire coating, an ocular implant, an auditory implant, a cochlear implant, a dental implant, a stimulator, a drug delivery depot, a filter, a membrane, a vascular access port, a stent, an envelope, a bag, a sleeve, intravenous or other tubing, a bag, a dressing, a patch, a fiber, a pin, a vascular graft, a suture, a cardiovascular suture, or an implantable prosthesis. In some embodiments, the medical device is a catheter such as, e.g., a vascular catheter, a urinary catheter, an intracranial catheter, an intraspinal catheter, a peritoneal catheter, a central nervous system catheter, a cardiovascular catheter, a drainage catheter, a soaker catheter, an aspirating catheter, an intrathecal catheter, a neural catheter, a stimulating catheter, or an epidural catheter. The catheter may be a vascular catheter such as, e.g., a central venous catheter, an arterial line, an pulmonary artery catheter, a peripheral venous catheter, an intravenous catheter, or an intraarterial catheter. In some embodiments, a surface of the polyurethane is coated with gendine, gardine, or chlorhexidine in a lower alkyl alcohol solvent. In some embodiments, minocycline and rifampin have been impregnated in the polyurethane using a solution that does not comprise a penetrating or alkalizing agent. In some embodiments, the medical device does not comprise a penetrating or alkalizing agent. The polyurethane may further comprise an additional therapeutic agent. The additional therapeutic agent may be impregnated in the polyurethane. In some embodiments, the additional therapeutic agent is coated on a surface of the polyurethane. The therapeutic agent may be an antimicrobial agent such as, e.g., chlorhexidine, gendine, or gardine. The additional therapeutic agent may be a thrombin inhibitor, a platelet inhibitor, an anti-inflammatory agent, an anti-fibrotic agents, or a vasodilator. In some embodiments, the additional therapeutic agent is argatroban, dipyridamole, a glyceryl nitrate or mercaptoethane sulfonate (MeSNA). MeSNA may be used to reduce or treat stricture, e.g., around a catheter. The additional therapeutic agent is calcium channel blocker, or an anti-arrhythmia drug such as, e.g., verapamil or thioridazine. In some embodiments, at least a portion of the medical device is coated with a hydrogel polyetherurethane. The hydrogel polyetherurethane may be a Tecophilic, TECOFLEX, or a polyurethane copolymer. In some embodiments, the medical device comprises polytetrafluoroethylene. In some embodiments, a surface of the medical device is coated or the device is impregnated with a chelator. In some embodiments, the chelator is calcium disodium EDTA. In some embodiments, the calcium disodium EDTA is comprised in an amount of about 0.01-1.5%, 0.1-1.5%, 0.5-1.5%, or 1-1.5% EDTA in a coating solution. The medical device may be a catheter such as, e.g., a drainage catheter or a vascular catheter. In some embodiments, the catheter is impregnated or coated with chlorhexidine. In some embodiments, the aliphatic polyether polyurethane polymer is coated on the surface of the medical device.

Another aspect of the present invention relates to a medical device comprising an aliphatic polyether polyurethane polymer having a durometer of A or B wherein the polyurethane is impregnated with chlorhexidine, gendine, or gardine. In some embodiments, the polyether polyurethane polymer is coated with a polyurethane coating comprising minocycline and rifampin. In some embodiments, the aliphatic polyether polyurethane is coated with a second polymer. The second polymer may be a polyurethane. In some embodiments, the aliphatic polyurethane is impregnated with chlorhexidine and gardine. In some embodiments, the aliphatic polyurethane is impregnated with chlorhexidine and gendine. In some embodiments, the aliphatic polyurethane is impregnated with chlorhexidine, gendine, and gardine. In some embodiments, the second polymer comprises minocycline and rifampin. In some embodiments, the polymer is a polyurethane such as, e.g., an aliphatic polyether polyurethane. In some aspects, the medical device may comprise an aliphatic polyether polyurethane polymer having a durometer of A or B wherein the polyurethane is impregnated with minocycline, rifampin, chlorhexidine, gendine, or gardine; wherein the polyurethane is coated with a second polyurethane (e.g., wherein the second polyurethane coating comprises minocycline and rifampin). In some embodiments, the polyurethane coating has a durometer of A or D, or the coating comprises a blend of A and D durometer aliphatic polyether-urethanes. The medical device may be a catheter. In some embodiments, the at least a portion of the medical device is coated with a hydrogel polyetherurethane. The hydrogel polyetherurethane may be a TECOPHILIC, TECOFLEX, or a polyurethane copolymer. In some embodiments, a surface of the medical device is coated or impregnated with a chelator such as, e.g., calcium disodium EDTA. The medical device may be a catheter such as, e.g., a drainage catheter or a vascular catheter. The catheter may be impregnated or coated with chlorhexidine. In some embodiments, the aliphatic polyether polyurethane polymer is coated on the surface of the medical device.

Yet another aspect of the present invention relates to a medical device, comprising a polymer impregnated with minocycline and rifampin, wherein a surface of the polymer is coated with a polymer coating comprising a fatty acid or a guanidium compound. The polymer coating may comprise a polyurethane, a silicone, a vinyl, a fluoropolymer, an olephin, or a polymer blend or copolymer thereof. In some embodiments, the polymer is polytetrafluoroethylene. In some embodiments, the polymer coating is a polyurethane coating. The polyurethane coating may have a durometer of A or D, or the coating may comprise a blend of A and D durometer aliphatic polyether-urethanes. The polyurethane may comprise chlorhexidine. The fatty acid may be caprylic acid (octanoic acid), caproic acid, lauric acid, or decanoic acid. In some embodiments, the fatty acid is capyrlic acid. The polymer coating may further comprises mercaptoethane sulfonate (MeSNA). The medical device may further comprise a thrombin inhibitor, a platelet inhibitor, an anti-inflammatory agent, an anti-fibrotic agents, or a vasodilator. The polymer may be a polyurethane, a silicone, a polyvinyl chloride (PVC), a fluoropolymer, or a polyester, or a copolymer or blend thereof. The at least a portion of the medical device may be coated with a hydrogel polyetherurethane. The hydrogel polyetherurethane may be a TECOPHILIC, TECOFLEX, or a polyurethane copolymer. The medical device may comprise polytetrafluoroethylene. The polytetrafluoroethylene may be TEFLON. A surface of the medical device may be coated or impregnated with a chelator such as, e.g., calcium disodium EDTA. The medical device may be a catheter such as, e.g., a drainage catheter or a vascular catheter. The catheter may be impregnated or coated with chlorhexidine. The aliphatic polyether polyurethane polymer may be coated on the surface of the medical device.

Another aspect of the present invention relates to an antimicrobial catheter, wherein the body of the catheter comprises an A durometer aliphatic polyether polyurethane polymer, wherein the polyurethane is impregnated with (i) minocycline and rifampin or (ii) chlorhexidine, gendine, or gardine. In some embodiments, the catheter is an antimicrobial catheter, wherein the body of the catheter comprises an A durometer aliphatic polyurethane polymer, wherein the polyurethane is impregnated with minocycline and rifampin. The aliphatic polyether polyurethane polymer may have a repeating unit of the formula: $[-O(CH_2)_n]_m-OC(O)NH-(CH_2)_x-NHC(O)-$; wherein n=1-4, x=1-10, m is less than 100 or 1-100, and m is greater than x, the repeating unit repeats 1-250 times, and the terminus of the polymer is hydrogen. In some embodiments, m is 1-100 or m is 1-50. In some embodiments, the repeating unit repeats 1-100 times. The at least a portion of the medical device is coated with a hydrogel polyetherurethane such as, e.g., a TECOPHILIC or a polyurethane copolymer. In some embodiments, a surface of the medical device is coated or impregnated with a chelator. The chelator may be, e.g., calcium disodium EDTA or a citrate. The catheter may be impregnated or coated with chlorhexidine. In some embodiments, the aliphatic polyether polyurethane polymer is coated on the surface of the medical device.

The polyurethane may further comprise a polymer coating (e.g., a polyurethane, a silicone, a polyvinyl chloride (PVC), a fluoropolymer, or a polyester, or a copolymer or blend thereof) comprising an additional therapeutic agent. The additional therapeutic agent may be an antimicrobial agent. The antimicrobial agent may be chlorhexidine, gendine, or gardine. The coating may comprise chlorhexidine and gendine. The coating may comprise chlorhexidine and gardine. The antimicrobial agent may be minocycline or rifampin. In some embodiments, the coating comprises minocycline and rifampin. The additional therapeutic agent may be a thrombin inhibitor, a platelet inhibitor, or a vasodilator. In some embodiments, the additional therapeutic agent is argatroban, dipyridamole, a glyceryl nitrate, or a thrombin inhibitor. The catheter may be a vascular catheter, a urinary catheter, an intracranial catheter, an intraspinal catheter, or an epidural catheter. In some embodiments, the catheter is a vascular catheter such as, e.g., a central venous catheter, an arterial line, an pulmonary artery catheter, a peripheral venous catheter, an intravenous catheter, or an intraarterial catheter.

Yet another aspect of the present invention relates to a method of catheterization comprising inserting a catheter of the present invention into a subject. The subject may be a mammal, such as a human.

Another aspect of the present invention relates to a method of producing an antimicrobial polymer, comprising: (a) contacting an aliphatic polyether polyurethane with a solution comprising a first lower alcohol and at least one antimicrobial agent for an amount of time sufficient to impregnate the minocycline and rifampin in the aliphatic polyether polyurethane; wherein the solution does not contain a penetrating agent or an alkalizing agent; and (b) substantially drying the aliphatic polyether polyurethane. In some embodiments, the method of producing an antimicrobial polymer, comprising: (a) contacting an aliphatic polyether polyurethane with a solution comprising a first lower alcohol, minocycline, and rifampin for an amount of time sufficient to impregnate the minocycline and rifampin in the aliphatic polyether polyurethane; wherein the solution does not contain a penetrating agent or an alkalizing agent; and (b) substantially drying the aliphatic polyether polyurethane. The at least one antimicrobial agent may be minocycline and rifampin. The at least one antimicrobial agent may be chlorhexidine. The at least one antimicrobial agent may further comprise gendine or gardine. The lower alcohol may be a $C_{1-6}$ alcohol such as, e.g., methanol, ethanol, propanol, butanol, or isopropanol. In some embodiments, the solution consists of the lower alcohol. The method may further comprise: (c) subsequent to step (a), coating at least a portion of a surface of the aliphatic polyether polyurethane with a second solution comprising: a second lower alcohol, a second organic solvent, and an additional therapeutic compound. The coating may be applied to substantially all of the external surfaces of the aliphatic polyether polyurethane. The second organic solvent may be an aliphatic ether solvent or a chlorinated solvent. The chlorinated solvent may be methylene chloride or chloroform. The aliphatic ether solvent may be tetrahydrofuran or diethyl ether. In some embodiments, the second lower alcohol is the same alcohol as the first lower alcohol. The second lower alcohol may be a $C_{1-6}$ alcohol such as, e.g., methanol, ethanol, propanol, butanol, or isopropanol. In some embodiments, the lower alcohol is methanol. In some embodiments, the solvent is tetrahydrofuran and the second lower alcohol is methanol. In some embodiments, the additional therapeutic compound is a second antimicrobial agent such as, e.g., minocycline, rifampin, chlorhexidine, gendine, or gardine. The additional therapeutic agent may be a thrombin inhibitor, a platelet inhibitor, an anti-inflammatory agent, an antifibrotic agent, or a vasodilator. In some embodiments, the additional therapeutic agent is argatroban, or dipyridamole. The additional therapeutic agent may be calcium channel blocker or an anti-arrhythmia drug such as, e.g., verapamil or thioridazine. In some embodiments, said coating has a durometer of A or D, or the coating comprises a blend of A and D durometer aliphatic polyether-urethanes. The aliphatic polyether polyurethane may have or comprise a repeating unit of the formula: $[-O(CH_2)_n]_m-OC(O)NH-(CH_2)_x-NHC(O)-$; wherein n=1-4, x=1-10, m is less than 500, and m is greater than x, the repeating unit repeats 1-250 times, and the terminus of the polymer is hydrogen. In some embodiments, m is 1-250 or 1-100. In some embodiments, the repeating unit repeats 1-100 times.

The resulting polyether polyurethane may have a durometer of A or B. The aliphatic polyether urethane polymer may be comprised in a medical device or a catheter.

In some embodiments, the aliphatic polyether urethane polymer is comprised in an endotracheal tube, a vascular catheter, a urinary catheter, a nephrostomy tube, a biliary stent, a peritoneal catheter, an epidural catheter, a central nervous system catheter, an intracranial catheter, an intraspinal catheter, an epidural catheter, an orthopedic device, a prosthetic valve, or a medical implant. The catheter may be a vascular catheter such as, e.g., a central venous catheter, an arterial line, a pulmonary artery catheter, and a peripheral venous catheter, an intraarterial catheter, or intravenous (i.v.) tubing.

Yet another aspect of the present invention relates to a method of producing an antimicrobial polymer, comprising: (a) contacting a polymer with a solution comprising a lower alcohol, minocycline, rifampin, and an alkalizing agent for an amount of time sufficient to impregnate the minocycline and rifampin in the aliphatic polyether polyurethane; (b) exposing the polymer to a neutralizing solution comprising an alkanoic acid for an amount of time sufficient to substantially neutralize the alkalizing agent; and (c) substantially drying the polymer. The alkalizing agent may be sodium hydroxide. The solution may further include a penetrating agent such as, e.g., ethyl acetate or butyl acetate. The polymer may be a polyurethane such as, e.g., an aliphatic polyether polyurethane. In some embodiments, step (b) comprises neutralizing a majority or substantially all of the alkylating agent. The lower alcohol may be methanol. The alkanoic acid may be a $C_{1-6}$ alkanoic acid such as, e.g., acetic acid, formic acid, propionic or butyric acid. In some embodiments, the $C_{1-6}$ alkanoic acid is acetic acid. The method may further comprise (d) subsequent to step (a), coating at least a portion of a surface of the aliphatic polyether polyurethane with a second solution comprising: a second lower alcohol, a second organic solvent, and an additional therapeutic compound. The coating may be applied to substantially all of the external surfaces of the aliphatic polyether polyurethane. The second organic solvent may be an aliphatic ether solvent or a chlorinated solvent. The chlorinated solvent may be methylene chloride or chloroform. The aliphatic ether solvent may be tetrahydrofuran or diethyl ether. In some embodiments, the second lower alcohol is the same alcohol as the first lower alcohol. In some embodiments, the second lower alcohol is methanol. In some embodiments, the solvent is tetrahydrofuran and the second lower alcohol is methanol. The additional therapeutic compound is an antimicrobial agent such as, e.g., chlorhexidine, gendine, or gardine. The additional therapeutic agent may be a thrombin inhibitor, a platelet inhibitor, an anti-inflammatory agent, an antifibrotic agent, or a vasodilator. In some embodiments, the additional therapeutic agent is argatroban, or dipyridamole. The additional therapeutic agent is calcium channel blocker or an anti-arrhythmia drug such as, e.g., verapamil or thioridazine. The coating may have a durometer of A or D, or the coating may comprise a blend of A and D durometer aliphatic polyether-urethanes. The aliphatic polyether urethane polymer may be comprised in a medical device or a catheter. In some embodiments, the polymer is comprised in an endotracheal tube, a vascular catheter, a urinary catheter, a nephrostomy tube, a biliary stent, a peritoneal catheter, an epidural catheter, a central nervous system catheter, an intracranial catheter, an intraspinal catheter, an epidural catheter, an orthopedic device, a prosthetic valve, or a medical implant. The catheter may be a vascular catheter such as, e.g., a central venous catheter, an arterial line, a pulmonary artery catheter, and a peripheral venous catheter, an intraarterial catheter, or intravenous (i.v.) tubing.

Another aspect of the present invention relates to a catheter comprising a polymer tubing, wherein the polymer tubing is an aliphatic polyether polyurethane polymer, a polyurethane polymer coated with an aliphatic polyether polyurethane polymer, or a polytetrafluoroethylene polymer coated with an aliphatic polyether polyurethane polymer; wherein the polymer is coated or impregnated with chlorhexidine, gendine, gardine, minocycline, and/or rifampin. The catheter may further comprise a second polymer coating on the polymer tubing. The second polymer coating may comprise an aliphatic polyether polyurethane. The coating may comprise chlorhexidine, gendine, gardine, minocycline, and/or rifampin. In some embodiments. The catheter may further comprise an additional therapeutic agent.

The low durometer polyether polyurethanes as described herein may be included on a surface of a medical device or may comprise a medical device such as a catheter. Exemplary medical devices include, e.g., an endotracheal tube, a vascular catheter, a urinary catheter, a nephrostomy tube, a biliary stent, a peritoneal catheter, an epidural catheter, a central nervous system catheter, an orthopedic device, a prosthetic valve, and a medical implant. The vascular catheter may be a central venous catheter, an arterial line, a pulmonary artery catheter, or a peripheral venous catheter. The central nervous system catheter may be an intraventricular shunt. Other medical devices that can benefit from the present invention include blood exchanging devices, vascular access ports, cardiovascular catheters, extracorporeal circuits, stents, implantable prostheses, vascular grafts, pumps, heart valves, and cardiovascular sutures, to name a few. The medical device may be a protection article such as a glove, mask, respirator, patch, foot cover, shoe liner, flip flop, ear plug, or nose plug. The medical device may be a structural implant such as penile implant, a cosmetic restorative or enhancement implant such as, e.g., a breast implant. In some embodiments, the medical device is a drainage tube or catheter, a shunt, a staple, a cord, a clip, a mesh, or a film.

In some aspects of the present disclosure, the medical device is prepared using an aliphatic polyether polyurethane polymer, a polyurethane polymer, or a polytetrafluoroethylene polymer. In some embodiments, any of the polymers are coated or impregnated with one or more therapeutic agent as described in this disclosure. Such therapeutic agents may include, but are not limited to, minocycline, rifampin, chlorhexidine, gendine, gardine, a fatty acid, another antimicrobial agent, a thrombin inhibitor, a platelet inhibitor, an anti-inflammatory agent, an anti-fibrotic agent, a vasodilator, a calcium channel blocker, an anti-arrhythmia agent, or a metal ion chelator. In some embodiments, the polymer is impregnated or coated with one, two, three, four, five, or six individual agents. In some specific embodiments, the polymer is coated with minocycline, rifampin, and chlorhexidine, gendine, or gardine. In some embodiments, the polymer is coated or impregnated with minocycline, rifampin, another therapeutic agent, and chlorhexidine, gendine, or gardine. In some embodiments, the polymer is coated with minocycline, rifampin, and another therapeutic agent. In some embodiments, the polymer is coated with chlorhexidine, gendine or gardine and another therapeutic agent. Additionally, in some aspects, the polymer is coated with a second polymer selected from an aliphatic polyether polyurethane polymer, a polyurethane polymer, or a polytetrafluoroethylene polymer before or after the polymer has been impregnated or coated with the above therapeutic agents. In some embodiments, the polymer is coated with a silicone, a vinyl, a fluoropolymer, an olefin, or blend of polymers thereof. The second polymer coating may itself be impregnated or coated with any of the above described therapeutic agents. In some embodiments, if the first polymer is polytetrafluoropolyethylene, then the polymer can be etched before being coated with a second polymer or coated or impregnated with a therapeutic compound.

The type of nosocomial infection that can be reduced or prevented in various embodiments include, but are not limited to, pneumonia, bacteremia, fungimia, candidemia, a urinary tract infection, a catheter-exit site infection, and a surgical wound infection. Nosocomial infections that can be reduced or substantially prevented may be caused by bacteria such as, e.g., drug resistant bacteria. Some non-limiting example of drug resistant bacteria include methicillin-resistant *staphylococcus*, vancomycin-resistant *enterococcus*, and resistant *Pseudomonas aeruginosa*. The nosocomial infection may be caused by a fungus such as, e.g., a drug resistant fungi. Examples of a drug resistant fungi include members of the *Candida* genus. Infection by other pathogenic organisms that can cause the nosocomial infections may be reduced or prevented by use of the methods and medical devices, such as catheters, as described herein.

In various aspects, the antimicrobial agents may reduce the growth of a wide variety of bacterial and fungal organisms. The bacteria may be spherical, rod-shaped, or spiral bacteria. Non-limiting examples of bacteria include staphylococci (e.g., *Staphylococcus epidermidis, Staphylococcus aureus*), *Enterrococcus faecalis, Pseudomonas aeruginosa, Escherichia coli*, among other gram-positive bacteria and gram-negative bacilli. Non-limiting examples of fungal organisms include *Candida albicans* and *Candida krusei*.

The term "organic solvent" as used herein refers to a solvent that can be used to dissolve antimicrobial agents. Organic solvents include alcohols (e.g., methanol, ethanol), ketones (e.g., acetone, methylethylketone), ethers (e.g., tetrahydrofuran), aldehydes (e.g., formaldehyde), acetonitrile, acetic acid, methylene chloride and chloroform.

The term "penetrating agent" as used herein refers to an agent or organic compound that is capable of promoting penetration of an antimicrobial agent, such as a guanidium compound, into the matrix of a polymer, such as a polyurethane, that may be present in or comprise a medical device. Non-limiting examples of such compounds are esters (e.g., ethyl acetate, propyl acetate, butyl acetate, amyl acetate, and combinations thereof), ketones (e.g., acetone and methylethylketone), methylene chloride and chloroform.

The term "alkalinizing agent" as used herein refers to organic and inorganic bases such as sodium hydroxide, potassium hydroxide, ammonia in water (e.g., 27% ammonium hydroxide), diethylamine and triethylamine.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, —[—$CH_2CH_2$—]$_n$—, the repeat unit is —$CH_2CH_2$—. In some embodiments of a repeating unit, the ends of the chains are capped with hydrogens. The subscript "n" denotes the degree of polymerization, that is, the number of repeat units linked together. When the value for "n" is left undefined or where "n" is absent, it simply designates repetition of the formula within the brackets as well as the polymeric nature of the material. In such a case, the polymer may contain one or more than one repeating units. The concept of a repeat unit applies equally to where the connectivity between the repeat units extends three dimensionally, such as in modified polymers, thermosetting polymers, etc.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
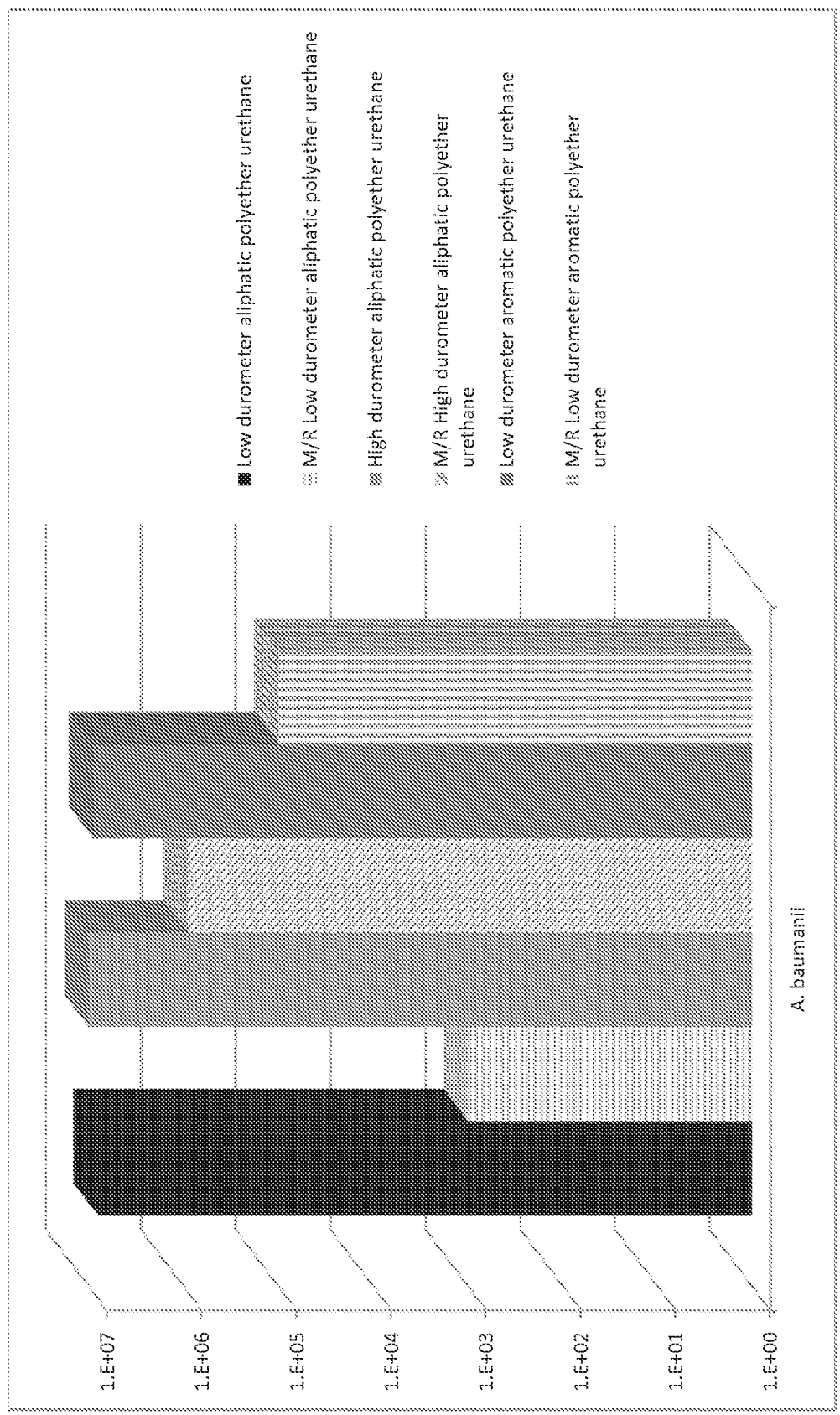
FIG. 1: Plot of Reduction in Adherent *Acinetobacter baumanii* (cfu/ml) to different polyurethane substrates Impregnated with M/R using only solvent and without penetrating or alkalizing agents.

Provided herein are medical devices and catheters comprising antimicrobial aliphatic polyether polyurethanes of durometer A or B. The aliphatic polyether urethane polymer may have a repeating unit of the formula: $[-O(CH_2)_n]_m-OC(O)NH-(CH_2)_x-NHC(O)-$; wherein n=1-4, x=1-12, and m is 1-100. In some embodiments, it has been observed that the polyurethanes may be impregnated and/or coated with antimicrobial agents without adversely affecting the flexibility of the resulting polymer. These antimicrobial polymers may be particularly useful in catheters, where flexibility and resistance to kinking or breakage is advantageous for clinical use.

The aliphatic polyether polyurethane polymer may be impregnated with one or more antimicrobial agents, such as minocycline and rifampin. In some embodiments, the polymer is coated with a polyurethane coating comprising an additional antimicrobial agent. The additional antimicrobial agent may be chlorhexidine, gendine, or gardine. As shown in the below examples, it has been observed that the impregnation of a polymer with minocycline, rifampin, and one of either: chlorhexidine, gendine, or gardine, can adversely affect the flexibility of the polymer over long-term storage. In contrast and as shown in the below examples, separating these antimicrobial agents in different layers of the polymer (e.g., impregnating minocycline and rifampin in the polymer and applying a separate coating containing chlorhexidine, gendine, or gardine) can result in antimicrobial polymers that display improved flexibility, mechanical properties, and resistance to kinking during longer-term storage.

Methods of producing antimicrobial aliphatic polyether polyurethanes are also provided. In some embodiments, an aliphatic polyether polyurethane may be impregnated with one or more antimicrobial agents by contacting the polyurethane with a solution comprising a lower alcohol and the antimicrobial agent(s), wherein the solution does not comprise a penetrating agent or an alkalizing agent. Exclusion of penetrating agents and alkalizing agents may in some embodiments promote retention of strength and flexibility of the polymer during longer term storage, e.g., over a period of weeks or months. In some embodiments, if it is desired to use an alkalizing agent, such as sodium hydroxide, to promote impregnation of an antimicrobial agent into a polymer, then the method may further comprise neutralizing the alkalizing agent. For example, after exposure to an alkalizing agent such as sodium hydroxide, the resulting polymer may be contacted with a solution of acetic acid to neutralize a majority of, or substantially all of, the sodium hydroxide that remains impregnated in the polymer. Neutralization of any remaining impregnated alkalizing agent in the polyurethane may also contribute to improved strength, flexibility, and resistance to kinking and/or breakage over longer term storage. As shown below in the examples, in contrast to methods which require heating to promote impregnation of an antimicrobial agent in a polymer, it has been observed that the polyether polyurethanes may be impregnated with an antimicrobial agent in a lower alcohol such as methanol at room temperature. Impregnating an antimicrobial at room temperature (e.g., 25-30° C.) without applying additional heating to the polymer may in some embodiments result in improvements to the strength and flexibility of the resulting polymer. Such improvements to the strength, flexibility, and resistance to kinking of the polymers may be beneficial for the clinical use of the polymers in medical devices such as catheters.

I. ALIPHATIC POLYETHER URETHANES

In some aspects, an aliphatic polyether polyurethane (also referred to herein as an "aliphatic polyether urethane polymer") may be included in a medical device such as a catheter. Sample chemical structures of the types of different polyurethanes are depicted below:

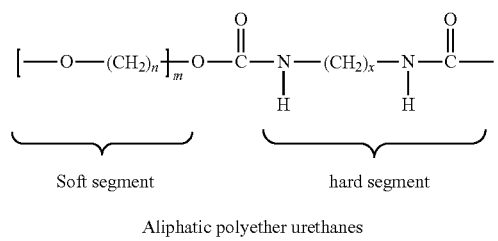

Aliphatic polyether urethanes

In some embodiments, n=1-4, x=1-12 and m is 1-100. In some embodiments, m is greater than x. n may be 1, 2, 3, or 4. x may be 1-6 or 1, 2, 3, 4, 5, 6, 7, 8, 9, 10, 11, or 12. In some embodiments, x=1-12, 1-10, 1-8, or 1-6. In some embodiments n=4 and x=6. Low durometer (softer) aliphatic polyurethane typically have a higher fraction of soft segments (m>x) and the high durometer polyurethanes have a higher proportion of hard segments (x>m). In some embodiments m=1-100, 1-99, 1-90, 1-80, 1-70, 1-60, 1-50, 1-40, 1-30, 1-20, or any range derivable therein. In some embodiments, the polymer has the formula $H[-O(CH_2)_n]_m-C(O)NH-(CH_2)_x-NHC(O)-H$. In some embodiments, the aliphatic polyether polyurethane is a low durometer polyurethane.

On the other hand, a typical aromatic polyether urethane chemical structure is depicted below:

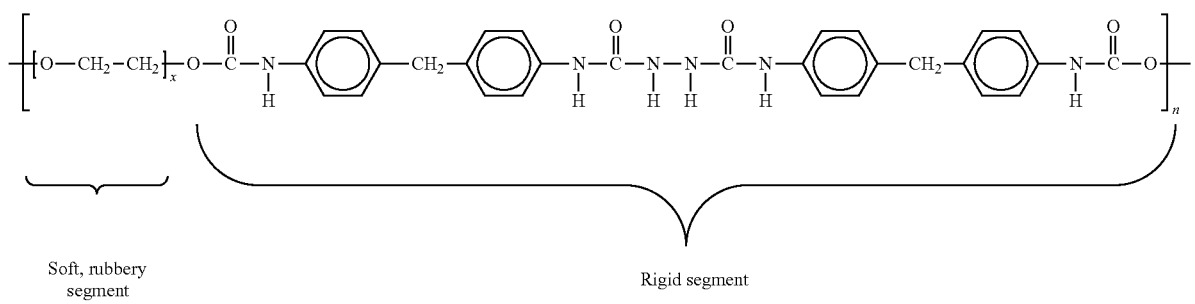

where, unlike in the aliphatic polyurethanes, the hard segments contain aromatic groups. Modifications of the exact chemical structure of the soft and hard segments from the sample structure above are possible. The durometer of the given polyurethane is governed by the relative proportion of soft and rigid segments.

As used herein, a "polyether polyurethane", "polyether urethane", or "polyether-urethane" may refer to an aliphatic polyether polyurethane, as described above.

A variety of copolymers or blends may be used with the present invention. In some embodiments, a polyurethane may be blended with another polymer. In some embodiments, minocycline and rifampin are impregnated into a polymer, copolymer, or polymer blend present in a medical device. These polymers, copolymers, and polymer blends include polyurethanes, polyvinylchlorides, silicones, polyesters, polyolephins and fluoropolymers. In some embodiments the polyurethane is a pellethane. In some embodiments, the polymer, copolymer, or blend is impregnated with minocycline and rifampin and then one or more of the surfaces of the polymer, copolymer, or blend is coated with chlorhexidine. The coating may comprise a co-dissolved polymer. The polymer may be a polyurethane. As described in further detail herein, the coating may be generated by exposing the polymer to a solvent, e.g., containing an additional therapeutic agent. Upon evaporation of the solvent, the polyurethane can dry to an adherent elastic coating. An uncured silicone can also be included in a coating. Subsequent to being applied, an uncured silicone may cure in situ to form an adherent elastic coating.

In some embodiments, the aliphatic polyether polyurethanes which can be formulated into a medical device include Lubrizol Tecoflex™ EG80A, EG85A, EG93A or EG100A, Bayer Duraflex® A4700 aliphatic ether TPU, Argotec® Argothane Aliphatic Polyether TPU 3751, or AdvanSource Biomaterials HydroSlip™ Hydrophilic Polyether Aliphatic Polyurethane. In some embodiments, Lubrizol Tecoflex™ EG93A can be formulated into a medical device. It is anticipated that a polyester including a polycaprolactone based polyurethane elastomer may be used instead of, or in combination with, a polyether polyurethane. The polyester based polyurethane elastomer may be an Estane™ In various embodiments, one or more of the following commercially available materials may be blended or otherwise used in various embodiments: Texin™, Desmopan™ (Bayer, Leverkusen, Germany); ChronoThane™, ChronoFlex™, HydroMed™, HydroThane™ (Advanced Biomaterials, Wilmington, Mass.); Quadrathane™, Quadraflex™ Quadraphilic™ (Biomerics, Salt Lake City, Utah). Polyurethanes of the current invention may also contain carbonate blocks, siloxane blocks, or silane derivatives.

A. Durometer and Polyurethane Hardness Scales

One property that reflects different polyurethane stiffness that arises from different monomer chemistries is durometer. Durometer measurement is defined in ASTM-D2240 and is a measure of material hardness through the depth of indentation generated by a given applied force using a specific tip geometry. Within the durometer system, there are numerous different scales used for different materials with different properties. Durometers measured on the A scale (for softer plastics) utilize a truncated conical tip and durometers measured on the D scale use a pointed conical tip. Durometer types A-D are traditionally used to denote the hardness of plastics with types A and D being the mostly commonly used. Type A referes to soft rubbers and plastics which can easily deform while type D is used to describe harder plastics, e.g., used to make bowling balls and hard hats. Within each type, the material is given a numeric subscore from 1-100 with 100 being the hardest material of that type and 1 being the softest. While the system has numerous different scales as outlined by the standard, the scales overlap so that a material with a type A 100 score would correlate with a type D score of 58. In some embodiments of the present invention, the hardness of the materials used to construct the medical device is type A-D durometer with a type A score of between 30 and 100. In some embodiments, the material has a hardness scored as a type A 93. In some embodiments, a polyether polyurethane, as described herein, has a durometer of A or B. In some embodiments, polyurethane is a low durometer or an A durometer polyurethane. The durometer polyurethane may be from 30A to 80D. In some preferred embodiments, the durometer of the polyurethane is from 80A to 95A.

B. Therapeutic Agents

A medical device, such as a catheter, may be impregnated or coated with one or more therapeutic agents. For example, the medical device or catheter may contain one or more antimicrobial agents, such as rifampin and minocycline, to help to decrease the incident of infections and adverse events. In some embodiments, the antimicrobial agents are incorporated into a surface of the medical device or catheter through impregnation of the polyether polyurethane. The therapeutic agent may be present in a coating or coated on the polymer surface.

In some embodiments, the polyether polyurethane surface or body of the medical device or catheter is impregnated with minocycline and rifampin. Rifampin is a bactericidal antibiotic drug of the rifamycin group. The IUPAC systematic name for rifampin is (7S,9E,11S,12R,13S,14R,15R,16R,17S,18S,19E,21Z)-2,15,17,27,29-pentahydroxy-11-methoxy-3,7,12,14,16,18,22-heptamethyl-26-{(E)-[(4-methylpiperazin-1-yl)imino]methyl}-6,23-dioxo-8,30-dioxa-24-azatetracyclo[23.3.1.14,7.05,28]triaconta-1(28),2,4,9,19,21,25(29),26-octaen-13-yl acetate. Minocycline may also be incorporated into the polyether polyurethane surface or body of the device. Minocycline is a broad spectrum tetracycline based antibiotic with an IUPAC systematic name of (2E,4S,4aR,5aS,12aR)-2-(amino-hydroxy-methylidene)-4,7-bis(dimethylamino)-10,11,12a-trihydroxy-4a,5,5a,6-tetrahydro-4H-tetracene-1,3,12-trione.

The polyether polyurethane surface or catheter be impregnated with chlorhexidine. Chlorhexidine (N',N''''-hexane-1,6-diylbis [N-(4-chlorophenyl)(imidodicarbonimidic diamide)]) is a small molecule antiseptic which can be effective against Gram-positive as well as Gram-negative bacteria. In some embodiments, chlorhexidine may be used in combination with, or may be substituted with, another antimicrobial guanidium compound such as, e.g., alexidine, hexamidine, polyhexamethylbiguanide or a chlorhexidine salt.

In some embodiments, a polyurethane polymer or catheter may be coated or impregnated with gendine or gardine. Gendine is a combination of both chlorhexidine and the dye, Gentian violet. Gentian violet is a triarylmethane dye which is good at impregnating different types of polymers. Additionally, other dyes, such as Brilliant Green and food safe dyes such FD&C Blue No. 1 and FD&C Yellow No. 5. When Brilliant Green is combined with chlorhexidine, the combination is called Gardine. These mixtures of dyes and chlorhexidine cause each compound to better impregnate the polymer leading to greater antibiotic efficiency and work with a wide range of different polymer formulations. A range of ratios of chlorhexidine to dye may be used, e.g., as described in U.S. Pat. No. 7,713,472.

A medium chain fatty acids or monoglyceride may be impregnated in or coated on a polymer as disclosed herein. The medium chain fatty acids or monoglyceride may have broad spectrum antimicrobial activity. Exemplary medium chain fatty acids that may be used include hexanoic, octanoic, decanoic and dodecanoic acids and their monoglycerides. The fatty acid may be a $C_{6-12}$ alkanoic acid or a $C_{6-10}$ alkanoic acid. Without wishing to be bound by any theory, the medium chain fatty acid or monoglyceride may enhance membrane permeability or otherwise disrupt membrane function in a microorganism such as a bacteria. The medium chain fatty acid or monoglyceride may be combined with one or more antibiotics such as, e.g., minocycline and rifampin. The fatty acid or monoglyceride may be incorporated into an emulsion, suspension, or solution in a polymeric coating as described herein. In some embodiments, the medium chain fatty acid or monoglyceride is applied onto one or more surfaces of a polymer, such as an aliphatic polyether polyurethane, that is impregnated with minocycline and rifampin.

In some embodiments, the polyether polyurethane surface or catheter comprises an anticoagulant, a platelet inhibitor, or a direct thrombin inhibitor. Impregnation of an anticoagulant in a catheter may reduce the probability of the catheter becoming clogged or occluded. Reducing the probability of catheter occlusion may be particularly desirable in embodiments where the catheter may be used intraarterially or intravenously. In some embodiments, agratoban is included on or impregnated in the polyether polyurethane surface or body. Argatroban is an anticoagulant with the IUPAC systematic name of (2R,4R)-1-[(2S)-5-(diaminomethylideneamino)-2-[[(3R)-3-methyl-1,2,3,4-tetrahydroquinolin-8-yl]sulfonylamino]pentanoyl]-4-methyl-piperidine-2-carboxylic acid]]. In some embodiments, dipyridamole may be included on or in the polyether polyurethane surface or body. Dipyridamole (2,2',2'',2'''-(4,8-di(piperidin-1-yl)pyrimido[5,4-d]pyrimidine-2,6-diyl)bis(azanetriyl)tetraethanol) can inhibit thrombus formation and promote vasodilation. In some embodiments a glycerol nitrate may be included on or in the polyether polyurethane surface or body. Glycerol nitrates can inhibit platelet activation (e.g., He'bert et al., 1997, Lacoste et al., 1994).

In some embodiments, the polyether polyurethane surface or catheter may contain a calcium channel blocker. Calcium channel blockers may increase the supply of blood and oxygen to the heart, and inclusion of a calcium channel blocker may be useful, e.g., for inclusion in catheters that may be used intraarterially or intravenously. The calcium channel blocker may be verapamil, amlodipine, nifedipine, diltiazem, thioridazine, or a thioridazine analogue. In some embodiments, the calcium channel blocker is a phenylalkylamine class L-type calcium channel blocker, such as, e.g., verapamil ((RS)-2-(3,4-dimethoxyphenyl)-5-{[2-(3,4-dimethoxyphenyl)ethyl]-(methyl)amino}-2-prop-2-ylpentanenitrile]]) or thioridazine (10-{2-[(R,S)-1-Methylpiperidin-2-yl]ethyl}-2-methylsulfanylphenothiazine]]). It is anticipated that a wide variety of therapeutic agents may be included in a catheter of the present invention. In some embodiments, the calcium channel blocker is impregnated in or coated on the aliphatic polyether polyurethane.

II. METHODS FOR PRODUCING CATHETERS AND POLYURETHANE SURFACES

A. Alkalizing Agents and Penetrating Agents

In some aspects, a polymer present in a medical device may be impregnated with one or more therapeutic agents without the use of an alkalizing agent or a penetrating agent. In some embodiments, the polymer is a low durometer polyether polyurethane present in a medical device such as a catheter. As described in further detail below in the Examples, the inventors have observed that use of a penetrating agent or an alkalizing agent can adversely affect the flexibility, strength, and/or susceptibility to kinking of a catheter. Catheters with reduced flexibility may have an increased likelihood of kinking and may be less suitable for clinical use. As described below, exposure of a polyurethane, such as a polyether polyurethane, to a solution comprising a lower alcohol (e.g., methanol) and one or more antimicrobial agents (e.g., minocycline and rifampin) can allow for impregnation of the antimicrobial agents into the polyurethane without the use of an alkylating agent or a penetrating agent.

Generally, an alkalizing agent can modify the bulk pH of the material by raising the pH. Alkalizing agents include hydroxide bases such as sodium hydroxide. A penetrating agent is an organic molecule which can be used to increase the polymers permeability, and may be used to enhance the ability of the molecules being added to the polyurethane to impregnate the polymer. Penetrating agents for the polyurethanes include nonpolar agents such as, e.g., ethyl or butyl acetate. Additional alkylating agents are described, e.g., in U.S. Pat. Nos. 5,624,704 and 5,902,283, which are incorporated herein by reference in their entirety.

Impregnation of an antimicrobial agent into an aliphatic polyether polyurethane may be accomplished by exposing the polyurethane to a solution comprising a lower alcohol, wherein the solution does not comprise a penetrating agent or an alkalizing agent. In some embodiments, the impregnation of one or more antimicrobial agents into a polyether polyurethane can be accomplished by exposing the polyether polyurethane to a solvent, such as a lower alcohol solvent (e.g., methanol, ethanol, butanol, isopropanol) comprising the antimicrobial agents (e.g., minocycline and rifampin) for about 1-600 minutes, 1-60 minutes, 1-30 minutes, 1-15 minutes, or 1, 2, 3, 4, 5, 6, 7, 8, 9, 10, 11, 12, 13, 14, or 15 minutes or any derivable range therein.

The impregnation reaction may be carried out at room temperature. In some embodiments, a low durometer polyether polyurethane may be impregnated with antimicrobial agent(s), such as minocycline and rifampin, in a lower alcohol solvent at room temperature. The impregnation reaction may occur at about 25-30° C., or 25, 26, 27, 28, 29, or 30° C., or any derivable range therein. Although in some embodiments, impregnation occurs at room temperature, it is nonetheless anticipated that a wider range of temperatures may be used, if desired. For example, the impregnation of antiseptic compounds and mixtures may occur at a temperature between about 25-50° C. After the impregnation of one or more antiseptics or antimicrobial agents, the polyurethane polymer may be more resistant to the colonization of bacteria such as *Pseudomonas aeruginosa*, e.g., as shown in the below examples.

B. Neutralization Method for Producing Catheters with Reduced Kinking

In some aspects, if it is desired to use an alkalizing agent to promote impregnation of an antimicrobial agent into a polymer, the method may further comprise a neutralization step to substantially neutralize a majority or substantially all of the alkalizing agent that may remain impregnated in the polymer. In some embodiments, inclusion of a neutralization step may be used to produce catheters with improved strength, flexibility, and/or resistance to kinking.

Although alkalinizing agents can increase impregnation of an antimicrobial agent, they may also reduce the strength and flexibility of the resulting polymer. For example, alkaline process aids such as sodium hydroxide can affect polyurethane catheter durability such that a stiff starting catheter composition is generally required to obtain a final catheter with sufficient mechanical strength. The use of a stiff starting catheter can make it more prone to kink upon flexure. As shown in the below examples, adding an acid neutralizing step following impregnation of antimicrobial agents (e.g., minocycline, rifampin, and/or chlorhexidine) may be used to promote neutralization of any residual alkalinizing agent in the catheter or medical device. In some embodiments, the neutralization step comprises washing the polyurethane in a solution comprising about 0.5-3% acetic acid.

Methods for using an organic solvent and a penetrating agent to impregnate polymeric devices with antimicrobial compositions, such as minocycline and rifampin, are described in U.S. Pat. Nos. 5,624,704 and 5,902,283, which are incorporated by reference herein in their entirety. An alkalinizing agent may be used to substantially enhance the extent of impregnation. The inventors have observed that when alkalizing agents are used with elastomeric polymer devices such as, e.g., a polyether polyurethane catheters, the incorporation of an acid neutralizing step, post-alkalinization, can substantially enhance the elasticity and reduce the stiffness of the resulting antimicrobial polyurethane device. In some embodiments, the alkalizing agent is sodium hydroxide, and the neutralization step comprises exposing the polymer to a solution of acetic acid for an amount of time sufficient to neutralize a majority of or substantially all of the impregnated sodium hydroxide.

In some embodiments, the following neutralization method may be used. A polyurethane catheter may be incubated at about 45° C. in a solution containing about 15% methanol/85% butyl acetate solution that further comprises one or more antimicrobial agents, such as minocycline and rifampin, and about 1% sodium hydroxide. After a 1 hour treatment, the catheter segments may be air flushed and then dried overnight at 60° C. The dried catheters may be washed repeatedly, e.g., triple washed, in deionized water containing 1% acetic acid. The catheter may then be dried again, e.g., for 4 hours at 60° C. Washing with a solution comprising a neutralizing agent may be performed for about from about 1 minute to 24 hours, from 1 minute to 1 hour, or about 1-15 minutes.

C. Sandwich Design for M/R/CH and Gendine/Gardine Catheters with Improved Kink Resistance and Stability As shown in the below examples, the combination of minocycline, rifampin, and chlorhexidine (M/R/CH) impregnated in catheters were observed by the inventors to display reduced stability over longer periods of storage. Without wishing to be bound by any theory, these results support the idea that this particular combination of compounds can, when simultaneously impregnated in a catheter or polymer, interact with the polymer to adversely affect the physical characteristics of the polymer. The inventors have observed that when these three components are simultaneously co-impregnated in a catheter (e.g., using the method of presaturating the catheter with chlorhexidine (CH) followed by impregnating with minocycline (M) and rifampin (R), as described in US20120064372) that over the course of several months storage at 25° C., a dull powdery substance can form along the surface. This formation is typically undesirable as it may impede insertion of the catheter and could serve as a source for thrombus formation.

In some embodiments, a polymer coating, optionally containing M, R or CH on both the lumenal and external surfaces, can reduce or substantially prevent migrating antimicrobial agents from reaching the surface. A polyurethane coating has been found to be the optimal coating for a polyurethane catheter and that a polyether urethane can be dissolved in volatile solvents and can be applied as a solution. Surprisingly, the external coating in conjunction with M/R/CH or Gendine/Gardine, particularly when comprising a blend of D and A durometer aliphatic polyether-urethanes, enhances kink resistance and elasticity.

In some embodiments, an aliphatic polyether polyurethane in a medical device, such as a catheter, as described herein may be impregnated with gendine, gardine, or chlorhexidine and coated with M and/or R. It is anticipated that a similar enhancements to kink resistance and elasticity may be observed in such catheters as compared to catheters impregnated with M and R and coated with gendine, gardine, or chlorhexidine. The coating may comprise A or D durometer aliphatic polyether-urethanes or a blend of D and A durometer aliphatic polyether-urethanes.

D. Simplified Method for Impregnating Aliphatic Polyether-Urethanes with M/R/CH or Gendine/Gardine Impregnating stiffer polyurethanes with M/R and optionally CH currently involves the use of a solvent, penetrating agent and preferably an alkalinizing agent. The process may take over 1 hour to complete. Using specific soft polyurethanes, the current invention provides in various aspects methods for producing catheters while omitting penetrating and alkalinizing agents. In some embodiments, an A durometer aliphatic polyether-urethanes may be impregnated with antimicrobial agents (e.g., M/R/CH, Gendine/Gardine, CH, or M/R) using only a solvent, such as a lower alcohol. Furthermore, the impregnation of these polymers can be accomplished in less than about 5 minutes. In some embodiments, the impregnation can be achieved in 1, 2, 3, 4 or 5 minutes or any range derivable thereof. In some embodiments, the impregnation can occur at room temperature. In some embodiments, the impregnation occurs at a temperature can be between 25 and 30° C. In some embodiments, the impregnation occurs at a temperature of 25, 26, 27, 28, 29 or 30° C., or any range derivable thereof. Because these methods may reduces the production time, the cost effectiveness of the catheter production may also be improved. Increasing the impregnation temperature can further reduce the time required for impregnation. The ability to exclude a penetrating and alkalinizing agent may reduce supply chain complexity, material and waste disposal costs, and processing costs.

Impregnating an A-durometer aliphatic polyether polyurethane with one or more antimicrobial agents (e.g., M/R/CH) may be accomplished using thermodynamically favorable mixing with the polymer and a solvent (e.g., a lower alcohol) containing the antimicrobial agent(s), without the inclusion of any penetrating agents, alkalinizing agents, or permeabilizing agents (e.g., sodium hydroxide) in the solvent. Aliphatic polyether-urethanes are commercially available from, for example, Lubrizol Corp under the Tecoflex™ brand. As shown in the examples below, minocycline and rifampin have been observed to be capable of rapidly impregnating a high polyether content (A durometer) Tecoflex™ with only the use of an organic solvent for the agents, such as a lower alcohol (e.g., methanol, ethanol). The solvent or lower alcohol may exert weak, reversible effects on polymer structure. This favorable combination of agent and polymer can avoid the need for an additional penetrating agent. When penetrating agents are used, the polymer may be substantially swollen, and mechanical benefits, such as orientation and crystalinity, may be substantially reduced or lost upon evaporation. Further, extruded or molded shapes can swell in thickness when a penetrating agent is used, making them stiffer in certain dimensions. The use of alkalinizing agents in combination with penetrating agents to impregnate polymeric devices may be deleterious to mechanical properties such as elasticity. These combinations of agents, solvents and polymers for impregnating preformed devices can result in a rapid, simple impregnating process with a reduced or minimal change to the underlying preformed device.

Additionally, in some embodiments, an impregnated polymer (e.g., impregnated with M/R) can be coated with polyether polyurethane, optionally containing one or more additional antimicrobial agents. In some embodiments, the device is coated by dipping the device into a solution of the polymer in an organic solvent or a solution comprising a permeabilizing agent and then removing the device to allow for drying. In some embodiments, the permeabilizing agent is an aliphatic ether, such as the solvent tetrahydrofuran (THF). The solution may have a concentration of about 1-25%, 1-10%, or about 1, 2, 3, 4, 5, 6, 7, 8, 9, or 10% or any derivable range thereof. In some embodiments, the device is allowed to dry overnight. The device may be allowed to dry for about 1-16 hours, 5-10 hours, or 5, 6, 7, 8, 9, 10 hours, or any derivable range therein. In some embodiments, the drying occurs at room temperature or at an elevated temperature to speed the drying process. The drying may occur at about 25-30° C., or 25, 26, 27, 28, 29, or 30° C., or any derivable range therein.

E. Single Step Combined Antithrombogenic—Antimicrobial Coatings

Thrombogenicity of catheters can present a problem with long-term implantations. Inhibition of thrombin activation may be used to reduce or prevent polymerization of fibrin. Heparin attachment to polymer surfaces may be used to reduce or prevent thrombin activation on intravascular polymeric devices. The processes to accomplish this are multi-step and complex because heparin is either insoluble or inactivated by exposure to non-aqueous fluids. Heparin attachment typically involves first attachment of a binding molecule or polymer to the surface, followed by activating it and exposure to aqueous heparin. The combination of heparin with antimicrobial agents such as chlorhexidine, gentian violet, brilliant green, minocycline and rifampin may be problematic since the coupling chemistries are generally incompatible with the agents. Surprisingly, the inventors have found that a different small molecule thrombin inhibitor, Argatroban, can be combined with these antimicrobial agents in a polymeric coating using common organic solvents compatible with M/R/CH/Gendine/Gardine such as methanol, butyl acetate, THF and halogenated organics. A lower alcohol such as methanol may be used to coat Argatroban onto a polymer or catheter surface. In some embodiments, the Argatroban solution composition comprises about 0.1-10%, 0.1-5%, or 0.1-2% Argatroban or any range derivable therein. In addition, further antithrombogenic protection can be accomplished by addition of a platelet activation inhibitor. The inventors have observed that dipyridamole can be compatible with the solvents used in the coating and impregnating systems for M/R/CH/Gendine/Gardine, and can also be readily combined with Argatroban and/or other antimicrobial agents in a single step coating to further reduce complications without introducing additional process complexity.

III. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation of M/R Impregnated Polyurethane Catheter Segments

One set of Polyurethane catheter segments (4 cm) were treated with Minocycline (M) and Rifampin (R) by treatment at 45° C. in a 15% methanol/85% butyl acetate solution containing 3% Rifampin, 1.5% Minocycline and 1% sodium hydroxide. After a 1 hour treatment, the catheter segments were air flushed and then dried overnight at 60° C. The dried catheters were triple washed in deionized water and then dried again for 4 hours at 60° C.

A second set of catheter segments was prepared in an identical manner to the first set except the sodium hydroxide concentration was reduced to 0.33% instead of 1% and the treatment time was 2 hours instead of 1 hour.

A third set of catheter segments was prepared in an identical manner to set number two except the wash steps were performed in 1% acetic acid solution.

Example 2

Polyurethane Coating of Impregnated Polyurethane Catheter Segments

A fourth set was of catheters was prepared in an identical manner to the third in Example 1. In addition, the surface was coated with polyurethane by briefly dipping in a 6% aliphatic polyether-urethane solution (Tecoflex® 93A, Lubrizol Corp) in tetrahydrofuran (THF) for this set of catheter segments. The coated catheter segments were dried at room temperature by hanging in a chemical fume hood overnight.

Example 3

Measurement of Flex Angle to the Onset of Kinking

The 4 cm long segments were tested for onset of kinking by fixing one end and slowly bending/rotating the other end. The onset of kinking was noted as the angle at which the bend point began to buckle. The angle was measured by protractor. The results of this analysis are shown below in Table 1.

TABLE 1

| Sodium hydroxide concentration | treatment time | rinse medium | Angle to onset of kinking |
|---|---|---|---|
| 0% (untreated control) | none | | 72 degrees |
| 1% | 1 hr | water | 83 degrees |
| 0.33% | 2 hr | water | 94 degrees |
| 0.33% | 2 hr | acetic acid | 103 degrees |
| 0.33% (polymer coated) | 2 hr | acetic acid | 125 degrees |

The greater the angle until the onset of kinking, then the more tolerant the catheter segment was towards bending/flexure.

Example 4

Chlorhexidine-Minocycline-Rifampin (CH-M-R) Treated Catheter Stability 4 cm long catheter segments were impregnated with CH-M-R by first presaturating in Chlorhexidine diacetate (4%) for 1 hour in 20% THF/80% methanol followed by treatment with 3% R, 1.5% M and 0.33% sodium hydroxide for 2 hours at 45° C. in 15% methanol/85% butyl acetate solution. Following drying, the segments were triple rinsed in 1% acetic acid solution and dried again. One set of samples was further coated by immersion in a solution of 7% Tecoflex® 93A containing 3% chlorhexidine in 70% THF/30% methanol followed by retraction within a few seconds and air drying.

The samples were allowed to age at ambient temperature. Following three weeks aging, a powder migrated to the surface of the impregnated catheter making it rougher and discolored. The polymer coated segments retained a shiny and smooth surface finish.

Example 5

Antimicrobial Impregnation of Low Durometer Aliphatic Polyurethane without Penetrating or Alkalizing Agents Tecoflex® 93A polyurethane was obtained from Lubrizol Corp. It was cast into cylindrical segments. The cylindrical segments were impregnated by exposing them to a solution of 15% Minocycline and 30% Rifampin in methanol for 2, 5, 10, and 15 minutes at room temperature. The segments were dried and then cross-sectioned to determine the extent of impregnation. Cylindrical segments were also impregnated with Gendine by exposure to a solution of 0.1% Gentian Violet and 4% chlorhexidine diacetate in methanol at room temperature. Impregnation was performed for 2, 5, 10, and 15 minutes. The segments were dried and then cross-sectioned to determine the extent of impregnation. Cylindrical segments were also impregnated with Gendine by exposure to a solution of 0.3% Gentian Violet and 4% chlorhexidine diacetate in methanol at room temperature. The segments were dried and then cross-sectioned to determine the extent of impregnation. Segments treated with methanol and no antimicrobial agents at 25° C. exhibited slight radial swelling (about 10-20%) and returned to their original diameters on drying.

Example 6

Antimicrobial Performance of Different Polyurethanes Impregnated with Minocycline/Rifampin (M/R) without the Use of Penetrating and Alkalizing Agents (with Only Solvent)

Impregnation of 3 different types of polyurethanes was attempted by immersing extruded segments in a solution of 15 mg/mL Minocycline and 30 mg/ml Rifampin in methanol at 20° C. for 30 minutes. Following impregnation, the segments were rinsed in water and then dried. The types of polyurethane impregnated were low durometer aliphatic polyetherurethane (Tecoflex® 93 A), high durometer aliphatic polyetherurethane (Tecoflex® 55D) and low durometer aromatic polyetherurethane (Tecothane® 95A). Controls were untreated segments of each of the types of polymers that were not impregnated.

Following a modified Kuhn's model of biofilm colonization [H. Hanna et al., 2006; R. Hachem et al., 2009], 1 cm long segments of uncoated control, and impregnated catheter segments were tested in triplicate for the inhibition of biofilm formation by a clinical isolate of *Acinetobacter baumannii* from our hospital. The segments were soaked for 24 hours at 37° C. in donor human plasma and then in serum at 37° C. for 1 week. Three individual segments of each type of catheter were then placed into sterile 24-well tissue culture plates containing 1 mL of $5.0 \times 10^5$ cfu/ml bacterial cells in Muller Hinton Broth and incubated for 24 hours. After incubation, the bacterial inoculum was discarded and segments washed by shaking for 30 min in 1 mL of 0.9% sterile saline. The segments were then removed with sterile sticks, placed in 5 mL of 0.9% saline and sonicated for 15 minutes. After sonication, each sample was vortexed for 5 seconds and 100 µL of sonicate liquid was serially diluted and plated onto Trypticase Soy Agar+5% Sheep Blood for quantitative culture. Plates were then incubated at 37° C. inverted for 24 hours and counted for colony growth. Results are presented in FIG. 1.

Example 7

Reduction in Adherent *Acinetobacter baumanii* (cfu/mL) to Different Polyurethane Substrates Impregnated with M/R Using Only Solvent and without Penetrating or Alkalizing Agents Only the low durometer aliphatic polyether urethane displayed a 4-log reduction in microbial attachment when no penetrating or alkalizing agents were used in the M/R treatments. High durometer aliphatic polyether urethane and low durometer aromatic polyether urethane gave a 2 log reduction or less in adherent organisms. This demonstrates that not all polyurethanes perform similarly when only a solvent (methanol) is utilized; hence the need to include penetrating (butyl actetate) and alkalizing agents (sodium hydroxide) in the prior art. We have surprisingly found that durable M/R antimicrobial protection (4-log reduction in adherent organisms) could be obtained for a specific subclass of polyurethanes (low durometer aliphatic polyether urethanes) with treatment only using a solvent and excluding the use of penetrating and/or alkalizing agents during treatment.

Example 8

Extent of Impregnation of Low Durometer Aliphatic Polyurethane Samples with M/R and Gendine without Penetrating or Alkalizing Agents Dried, impregnated polyurethane cylinders from example 4 were cross sectioned using a scalpel. All the M/R samples had turned reddish all the way through the crosssection. The 2 minute Gendine exposed samples turned light violet through the cross-sections, the samples immersed 5 minutes or longer turned dark violet in color.

Samples were stretched in tension. The M/R samples treated for longer than 5 minutes had appreciably lower tensile strengths (extended with application of much less force) than the 5 minute or less exposed samples. The 2 minute, 0.1% Gendine sample required a similar force as a methanol treated control; the 5 minute and longer samples stretched more easily. The 0.3% Gendine samples showed a similar time extension behavior. The easier extension indicates plasticization of the aliphatic polyetherurethane by the antimicrobial agents following evaporation of the solvent.

The surfaces of the Gendine samples were softer and tackier than the surface of the methanol controls.

Example 9

Polyurethane Coating of Gendine Impregnated Aliphatic Polyetherurethane Segments The 5 minute 0.3% Gendine impregnated segments were further coated with a mixture of 6% Tecoflex® 93A and 3% 60D. The coating solutions further contained 4% chlorhexidine diacetate and 0.1% Gentian violet in 60% THF/40% methanol. The coating was performed by dipping the cylinder into the coating solution followed by retraction within a few seconds. The coated and impregnated segment was dried overnight at ambient temperature in a chemical fume hood.

Example 10

Tensile Elongation of Gendine Aliphatic Polyetherurethane Segments

The 93A-60D blend had a less tacky surface (harder) than the 93A only coating solution. Extension was further measured when a 1.25 kg weight was suspended from the end of the 93A-60D coated segments. The results are shown below in Table 2.

TABLE 2

| Impregnation Treatment | Coating | % Elongation |
|---|---|---|
| control | none | 76% |
| 5 minutes 0.3% Gendine in methanol | none | 100% |
| 5 minutes, 0.3% Gendine in methanol | polyurethane/Gendine | 83% |

The coating nearly restored the original tensile properties of the Gendine impregnated sample. The coated sample was less tacky and firmer than the Gendine samples in Example 6.

Example 11

Preparation of Coating Solution Containing Argatroban

The coating solution described in Example 9 further had Argatroban Monohydrate dissolved at 1% concentration. A non-tacky, smooth coating resulted on the catheter surface following immersion, retraction and drying.

Example 12

Comparison of M/R High Durometer Aliphatic Polyurethane Catheters Prepared with Solvent, Penetrating and Alkalizing Agents with M/R Low Durometer Aliphatic Polyurethane Catheters Prepared Using Solvent Only Catheter segments were prepared from low durometer polyetherurethane by the methanol immersion method in Example 6 except impregnation was for 60 minutes. M/R high durometer polyurethane catheter segments were also prepared by the method in U.S. Pat. Nos. 5,624,704 and 5,902,283 employing penetrating agent (butyl acetate), solvent (methanol) and alkalizing agent. Controls were segments of both types of polyurethane that were M/R treated.

Microbiological Baseline Testing: Segments were tested in triplicate for ability to resist colonization by *Acinetobacter baumanii*. Segments were placed into sterile 24-well tissue culture plates containing 1 ml of human donor plasma for 24 hr to simulate the binding of blood proteins and incubated at 37° C. The plasma were then replaced with $5.0 \times 10^5$ cells in Muller Hinton Broth of *A. baumanii* incubated for an additional 24 h. After incubation, the bacterial inoculum was discarded and segments were washed by shaking for 30 min in 1 ml of 0.9% sterile saline. The segments were then removed with sterile sticks, placed in 5 ml of 0.9% saline and sonicated for 15 min. After sonication, each sample was vortexed for 5 s and 100 µl of liquid from each segment was serially diluted and plated onto Trypticase Soy Agar+5% Sheep Blood for quantitative culture. Plates were then incubated at 37° C. for 24 h and counted for colony growth.

Microbiological Durability Testing: To test the durability of prolonged inhibition of biofilm formation in a simulated physiologic environment, control and M/R catheter segments were further incubated in serum at 37° C. for 1 week and then challenged with *A baumanii* inoculum as described above. Another set was incubated for two weeks and another for 3 weeks (serum replaced weekly). *A. baumanii* challenges for each additional set of incubated catheter segments were performed as described above.

Figure 2:
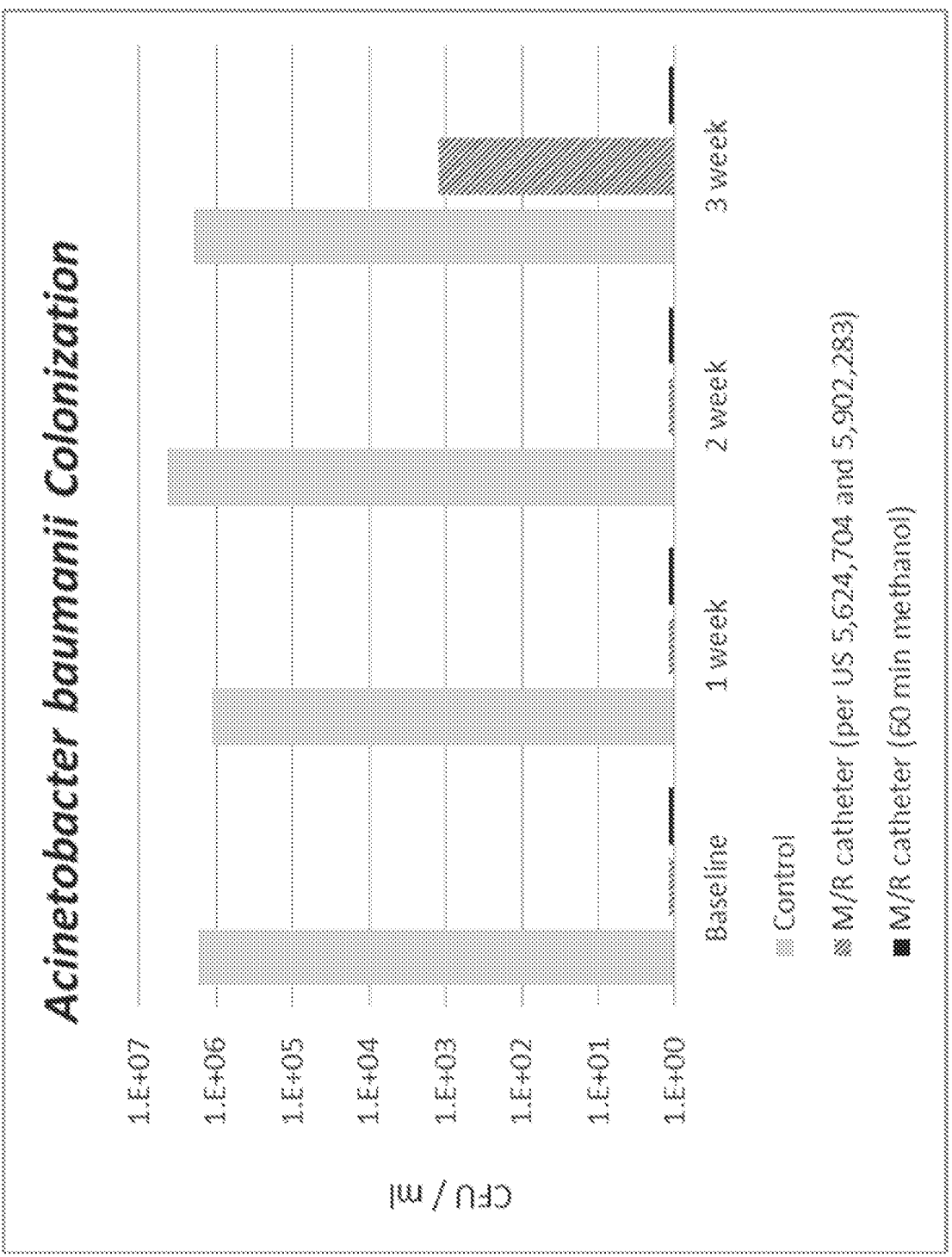
FIG. 2: Plot of *Acinetobacter baumanii* colonization on a control, catheter treated by methods in U.S. Pat. Nos. 5,624,704 and 5,902,283, and the current method (60 minutes in methanol).

Quantitative *A. baumanii* recoveries are reported below for baseline, 1 week, 2 weeks and 3 weeks. The control catheters (different polyurethane base materials) gave nearly identical results so an average control is reported in FIG. 2.

At 1 week, the 60 minute methanol impregnation was able to completely prevent *A. baumanii* colonization demonstrating improved durability over the 30 minute treatment in Example A. The complete prevention of *A. baumanii* colonization was retained through 3 weeks. Performance of the M/R catheter prepared with solvent, penetrating agent and alkalizing agent was similar through 2 weeks but breakthrough *A. baumanii* adherence occurred at week 3. The methanol (solvent only) M/R impregnation of the low durometer aliphatic polyurethane demonstrated equivalent or superior performance at each time point to the M/R catheters prepared with higher durometer polyurethane using the solvent, penetrating and alkalizing agent method described in U.S. Pat. No. 562,474 and U.S. Pat. No. 5,902,283.

Example 13

Sandwich CH Coating on Solvent Only (Methanol) Impregnated M/R Catheter

Low durometer aliphatic polyurethane catheter segments were impregnated with M/R by immersion in a methanol solution (15 mg/ml Minocycline, 30 mg/ml Rifampin) as in Example 12, rinsed and dried. A portion of the M/R segments were further sequentially coated with chlorhexidine diacetate (CH) as follows:

Lumen coating: Lumens of dried impregnated catheters will be coated by mixing CH dissolved in methanol into aliphatic polyurethane dissolved in tetrahydrofuran. The final coating solution consist of 8 mg/ml CH, 1.5% polyurethane polymer in a mixed 30% Methanol/70% tetrahydrofuran solvent. The coating solution was injected through the catheter lumen and immediately air flushed/dried to dry and create a smooth lumenal surface.

External coating: After lumen coating and drying, catheters were coated externally using a more concentrated CH solution with aliphatic polyurethane polymers. The final external coating solution comprised 42 mg/ml CH and 11% polyurethane in 30% Methanol/70% tetrahydrofuran mixed solvent. The external coating is applied by rapidly dipping then retracting the catheter followed by hanging to air dry overnight to leave a smooth surface finish.

Catheter segments with only the CH lumen and external coatings (no M/R) were prepared as well. Additional controls were untreated catheter segments.

Figure 3:
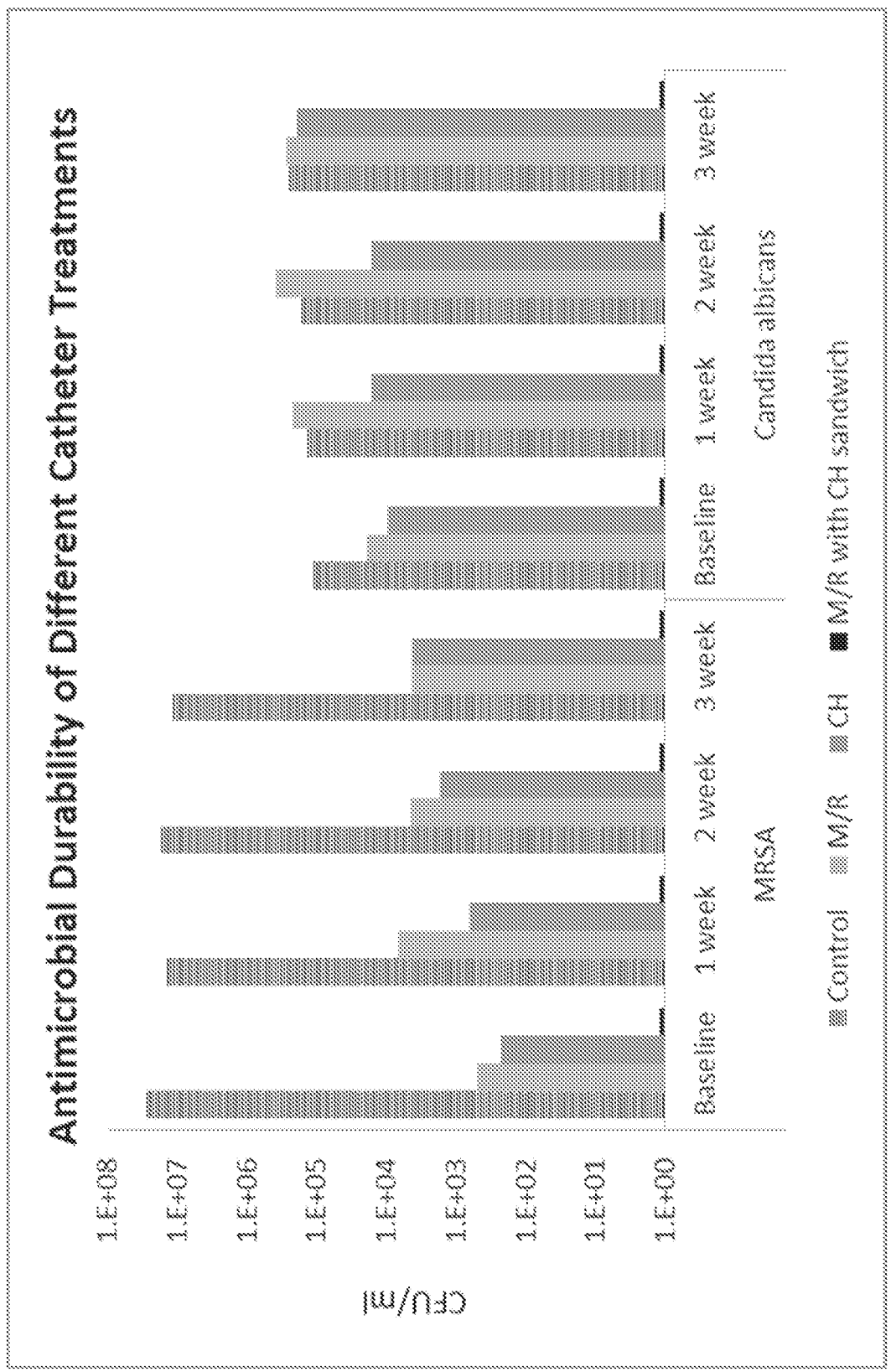
FIG. 3: Antimicrobial durability of different catheter treatments.

Ability of the catheters to resist colonization by clinical isolates of Methicillin Resistant *Staphylococcus aureus* (MRSA) and *Candida albicans* were tested using the microbiological method described in Example 12. Results for both baseline and durability are shown in FIG. 3.

Only the M/R catheters with CH sandwich coating were able to completely inhibit MRSA and *C. albicans* colonization for 3 weeks. The M/R catheter with CH sandwich coating demonstrated superior performance to M/R alone or CH alone at each time point.

Example 14

Gendine Sandwich Coating

Figure 4:
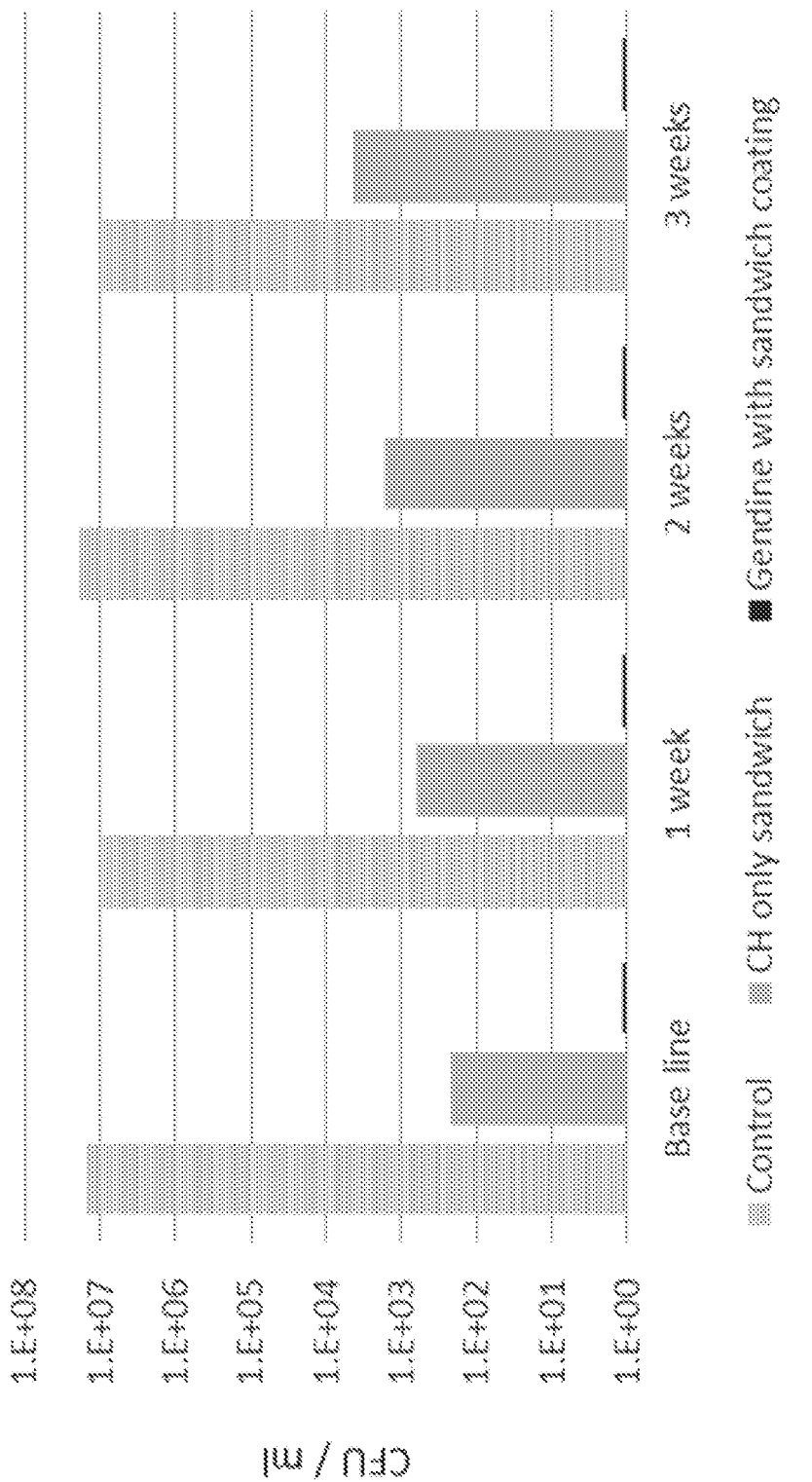
FIG. 4: Antimicrobial durability of Gendine sandwich coating against MRSA.
Figure 5:
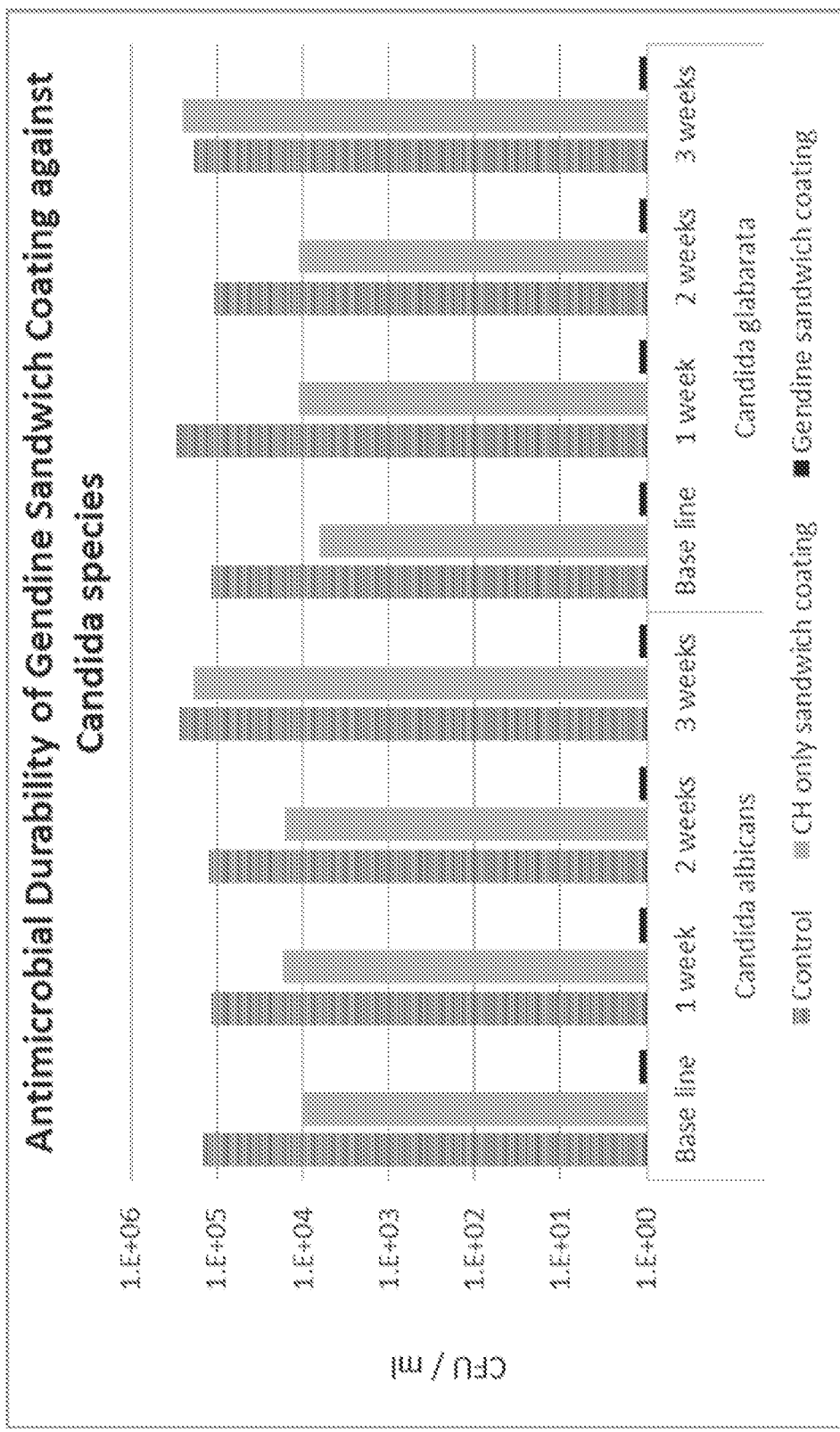
FIG. 5: Antimicrobial durability of Gendine sandwich coating against *Candida* species.

Gendine low durometer aliphatic polyurethane catheter segments were prepared as described in Example 5. A sandwich Gendine coating of the lumen and external surfaces was prepared as described in Example 13 except the lumen coating solution in addition to CH also contained 0.02% Gentian Violet. The external coating solution in addition to CH also contained 0.1% Gentian Violet. Controls were untreated catheter segments and segments sandwich coated with CH only (as in example 13). Antimicrobial durability was tested as in Example 13. Results for MRSA challenges are shown by FIG. 4. Results for *Candida albicans* and *Candida glabarata* are presented in FIG. 5. These results show that the Gendine catheters prepared by sandwich coating is highly effective and outperforms CH alone at each time point for each challenge organism.

Example 15

Gendine Sandwich Coated Teflon® Catheter

Figure 6:
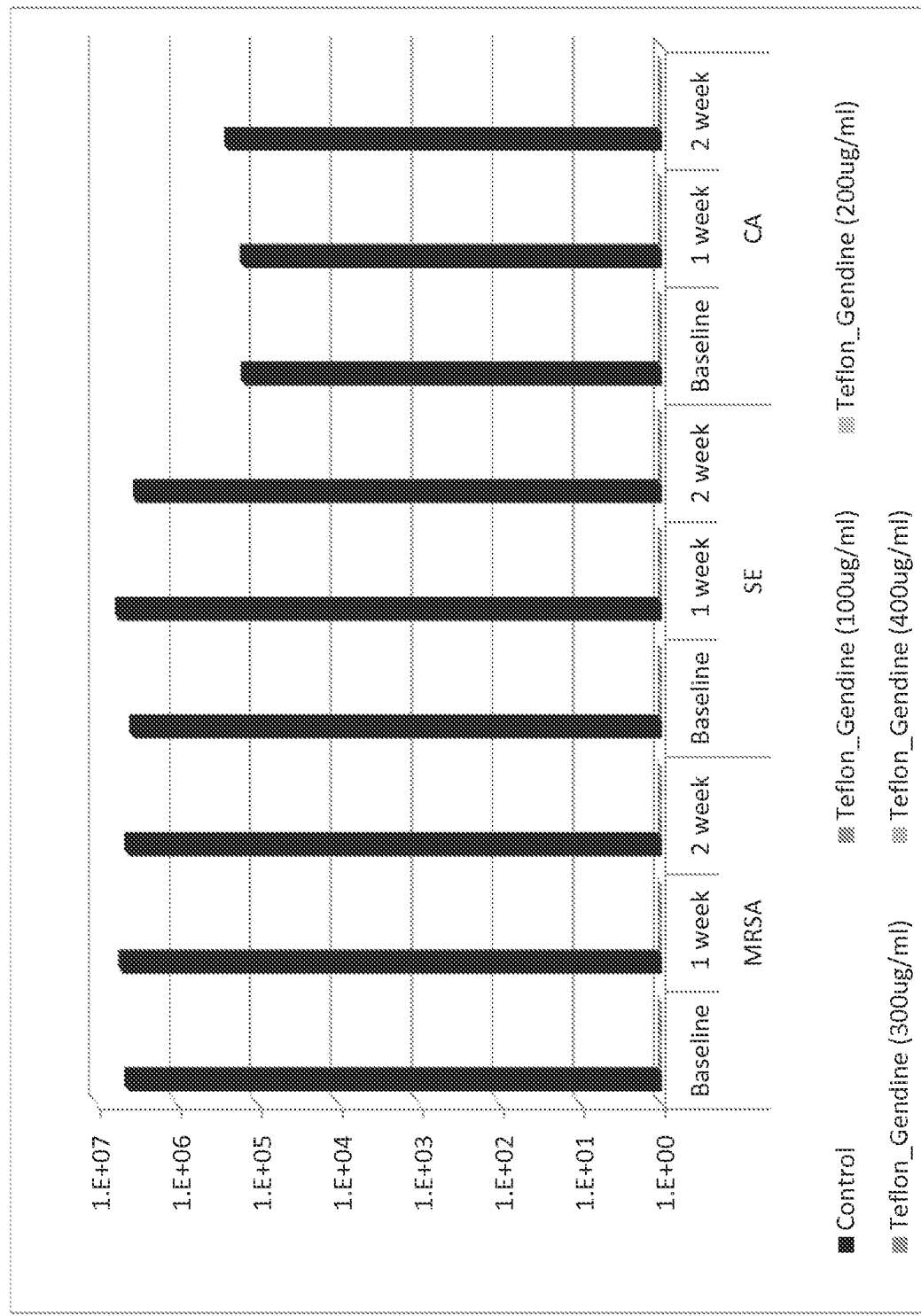
FIG. 6: Antimicrobial durability of Gendine sandwich coated Teflon® catheters against MRSA, *Staphylococcus epidermidis* (SE), and *Candida* (CA).

Teflon catheters were thoroughly cleaned with methanol and dried. Catheters were warmed to 40-50° C. Catheters were then immersed in a warm (50-60° C.) Fluoroetch solution for 2-3 minutes. Catheters were immediately rinsed in methanol for 15 seconds and then in hot (70° C.) deionized water for 30 seconds followed by rinsing in hot (70° C.) deionized water-acetic acid (2-5%) solution (pH 4) for 1 minute. Catheters were thoroughly dried. Catheters were coated gendine polyurethane solution as in Example 9 with the modification that reduced Gentian Violet concentrations ranging from 0.04% (400 ug/ml) to 0.01% (100 ug/ml) were used. The antimicrobial performance of the gendine coated TEFLON catheters are shown below in FIG. 6.

Example 16

Hydrogel Coated Catheters

The hydrogel coated catheters described in Examples 13 and 14 were further tested below with the following modifications.

Second Coating Step Addition

Catheters of Example 14 were spray coated with an additional surface layer of hydrogel poyetherurethane (Tecophilic® polyurethane, Lubrizol Corp.) in THF solvent and polyvinylpyrrolidone in water-methanol. Following drying, the samples were manually tested for frictional resistance by sliding wetted latex gloved finger tips along the catheter surface. Hydrogel coated catheters were noticeably more lubricious than without.

Single Coating Step Incorporation

The external coating of Example 13 was prepared with a blend of aliphatic polyurethane and hydrogel polyetherurethanes (Tecophilic® polyurethane, Lubrizol Corp). Coatings were prepared with blend ratios of 0:100, 1:99, 10:90, 25:75, 50:50, 75:25, 90:10 and 100:0 and with total polyurethane concentrations ranging from 5 to 11%. Following drying, the coatings were manually tested for frictional resistance by wetting latex gloved finger tips and sliding over the surfaces. Blended coatings with 10% or more hydrogel polyetherurethane were noticeably more lubricious than the others.

Figure 7:
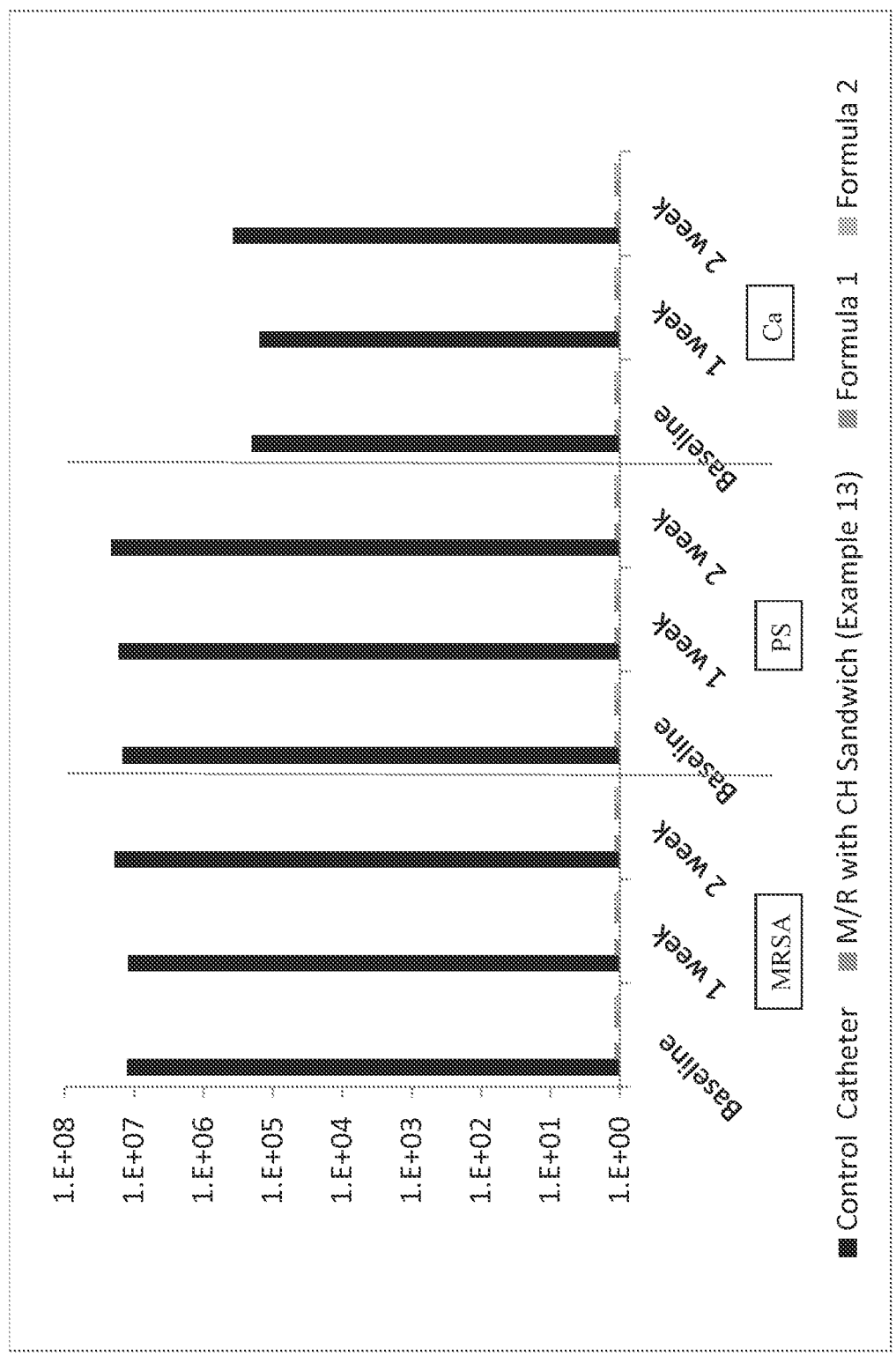
FIG. 7: Antimicrobial durability of catheters against MRSA, *Pseudomonas aeruginosa* (PS), and *Candida albicans* (Ca).

External coatings as in Example 13 were prepared using a solution with 2.4% CH, 2.3% Tecoflex® 60D, 1.5% Tecoflex® 93A and 1.5% Tecophilic® 93A (Formula 1) and 2.4% CH, 3% Tecoflex® 60D and 3% Tecophilic® 60D (Formula 2). Antimicrobial durability was tested against MRSA, *Pseudomonas aeruginosa* (PS), and *Candida albicans* (Ca) by the method described in Example 12. Results are shown in FIG. 7. The Tecophilic® containing coatings with reduced CH and polymer concentrations showed no reduction in antimicrobial performance relative to the catheter of Example 13.

Example 17

Impregnation with Minocycline-Rifampin and Chelator

Figure 8:
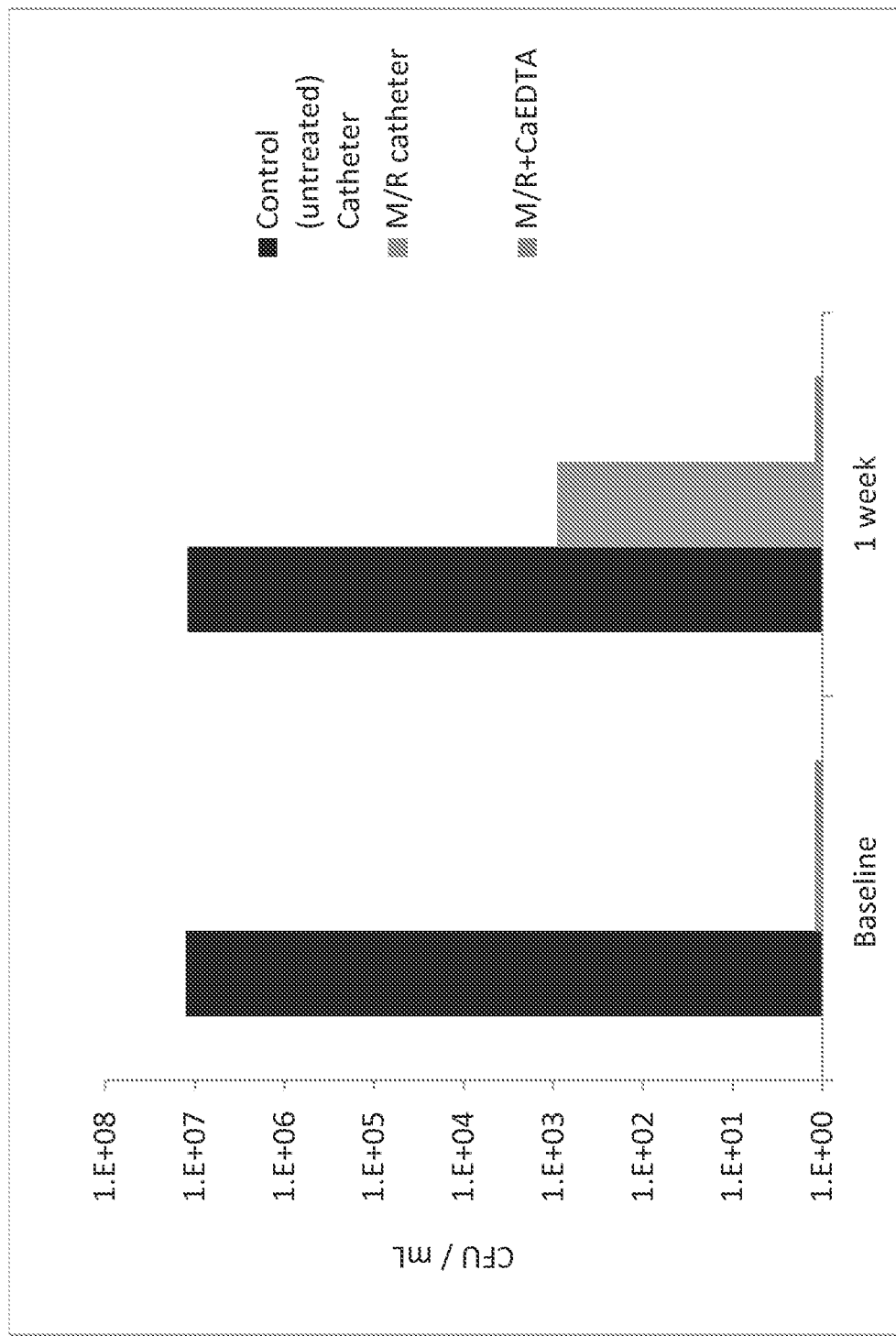
FIG. 8: Inhibition of MRSA colonization by catheter coatings.

Catheters were impregnated as in Example 12. For some catheters the impregnation solution also contained the chelator calcium disodium ethylenediaminetetraacetic acid (CaEDTA) co-dissolved in methanol at a concentration of 1.5% (M/R+CaEDTA). Catheters were tested for 1 week antimicrobial durability against MRSA using the methods described in Example 12. Controls were catheters prepared as in Example 12. Results are shown below in FIG. 8. The M/R+CaEDTA catheter demonstrated improved antimicrobial durability over the M/R catheter.

Example 18

Sandwich Coated Minocycline-Rifampin and Chelator Catheters

Figure 9:
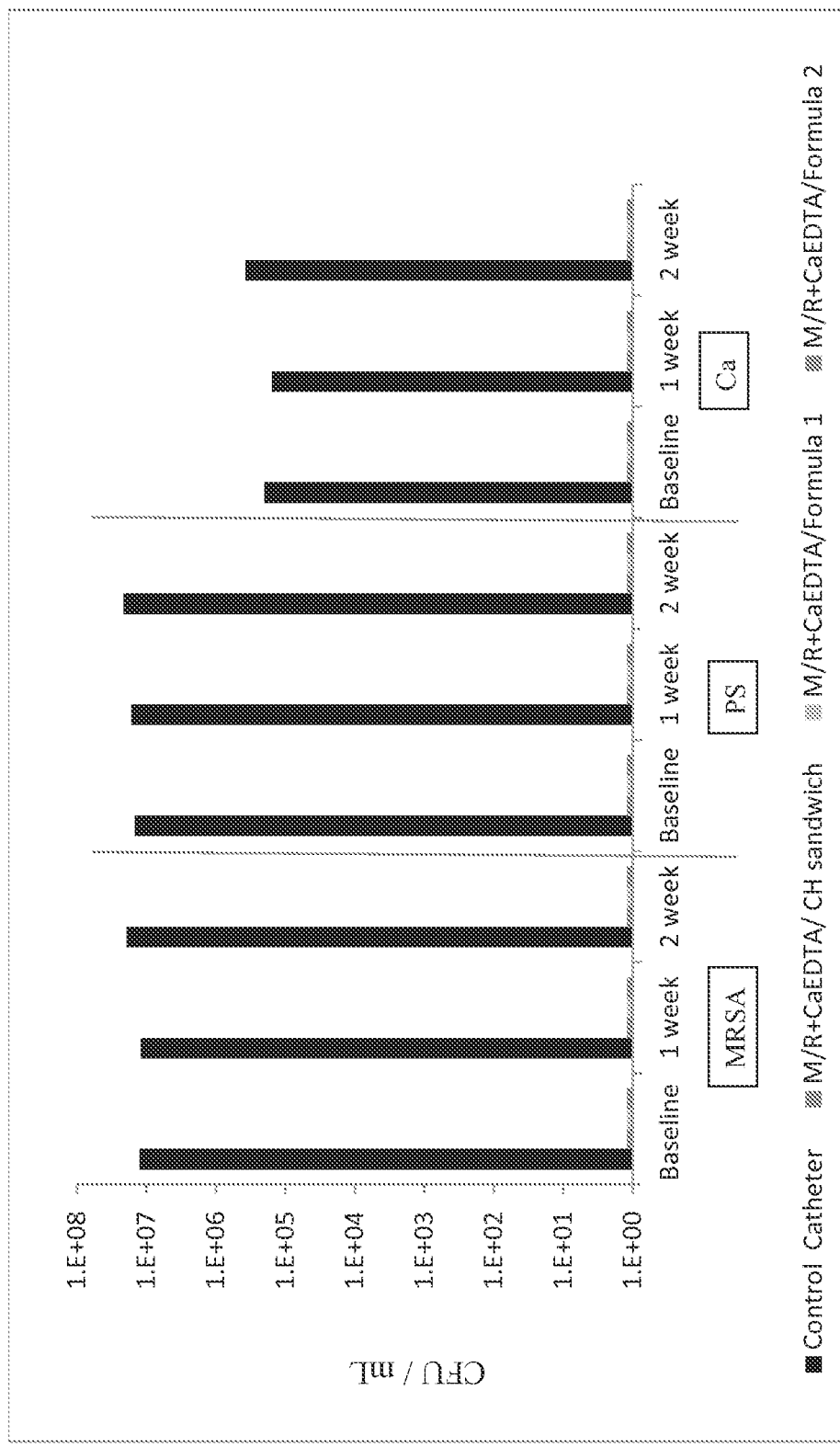
FIG. 9: Antimicrobial durability of catheters containing against MRSA, *Pseudomonas aeruginosa* (PS), and *Candida albicans* (Ca).

Minocycline-Rifampin (M/R)+chelator (calcium ethylenediaminetetraacetic acid, "CaEDTA") impregnated catheters were prepared as described in Example 17, and these catheters were further coated as described in in Example 13 (M/R+CaEDTA/CH sandwich) and Example 16 (M/R+CaEDTA/Formula 1 and M/R+CaEDTA/Formula 2; using the single coating step incorporation). Antimicrobial durability was tested using the test as described in Example 16 (single coating step incorporation). Results are shown below in FIG. 9. For the M/R+CaEDTA catheters, the Tecophilic® containing coatings with reduced chlorhexidine (CH) and polymer concentrations showed no reduction in antimicrobial performance relative to the CH sandwich coating of Example 13.

Example 19

Drainage Catheters

Figure 10:
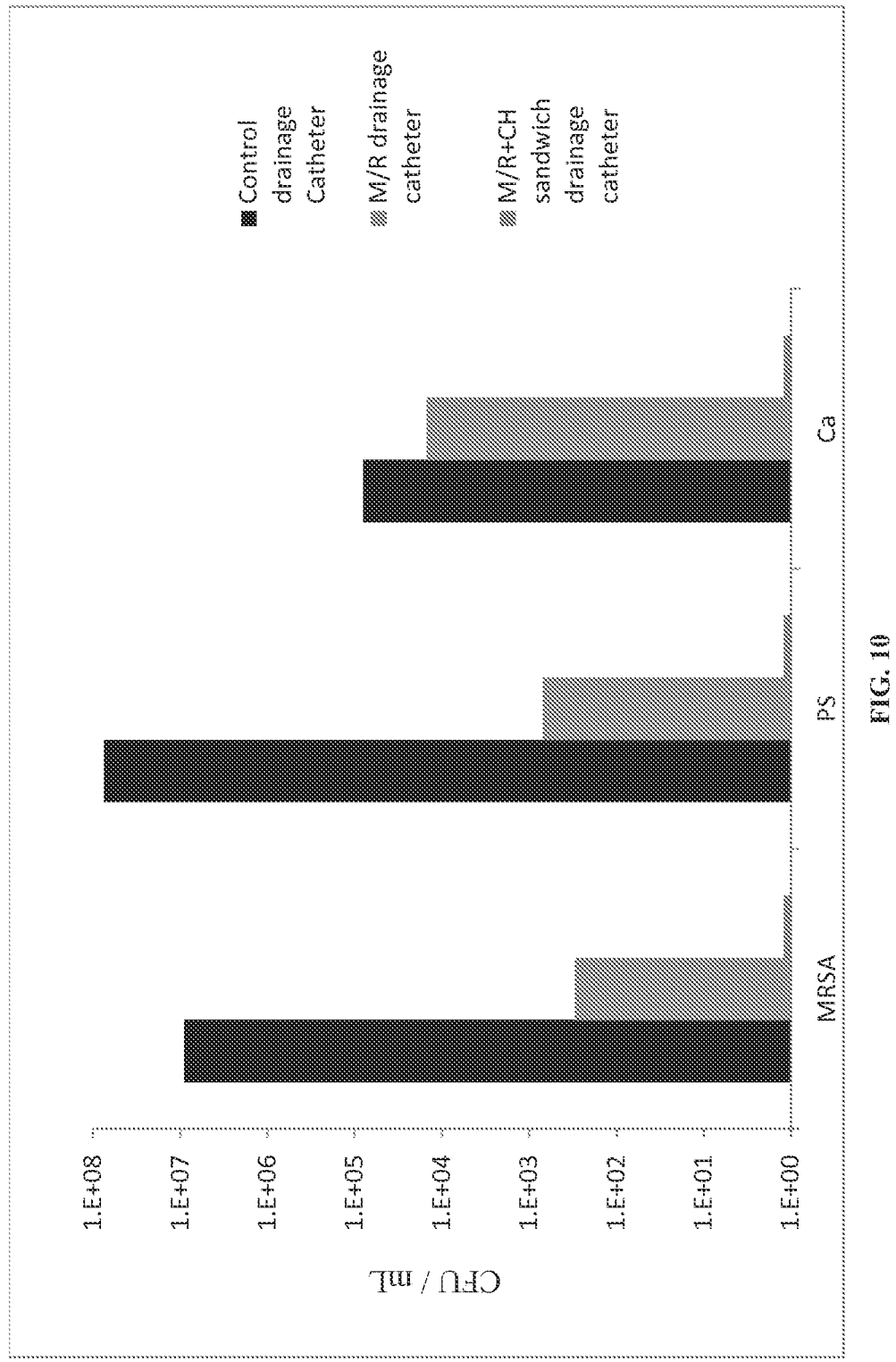
FIG. 10: Antimicrobial durability of drainage catheters against MRSA, PS, and Ca.

Surgical drainage catheters fabricated using Tecoflex® 93A. Some were subsequently treated with M/R as described in Example 12. Some of the catheters were additionally sandwich coated with chlorhexidine (CH) as described in Example 13. Baseline microbiological testing was performed as in Example 12 against MRSA, PS and Ca. Results are shown below in FIG. 10. The drainage catheters showed similar antimicrobial performance for the M/R and M/R+CH sandwich treatments to the vascular catheters.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,624,704
U.S. Pat. No. 5,902,283
R. Hachem et al. *Antimicrob. Agents Chemother,* 53(12): 5145-5149, 2009.
H. Hanna et al. *Antimicrob. Agents Chemother,* 50(10): 3283-3288, 2006.
He'bert et a., "Persistent Inhibition of Platelets During Continuous Nitroglycerin Therapy Despite Hemodynamic Tolerance" *Circulation,* 95: 1308-1313, 1997.
Lacoste et al., "Antithrombotic properties of transdermal nitroglycerin in stable angina pectoris" *The American Journal of Cardiology Volume* 73, Issue 15, p. 1058-1062, 1994.

The invention claimed is:

1. A medical device comprising:
   (A) a first antimicrobial polymer layer comprising an aliphatic polyether polyurethane polymer having a durometer of A or B that has been solvent impregnated with minocycline and rifampin, but has not been solvent impregnated with chlorhexidine; and
   (B) a second antimicrobial polymer layer formed from a polymer coating solution comprising chlorhexidine; wherein the polymer coating solution does not comprise minocycline or rifampin;
   and wherein the medical device is a catheter.

2. The medical device of claim 1, wherein the aliphatic polyether polyurethane polymer has a durometer of A.

3. The medical device of claim 1, wherein the polymer coating solution comprises gendine, gardine, and chlorhexidine.

4. The medical device of claim 1, wherein the polymer coating solution comprises a lower alcohol.

5. The medical device of claim 1, wherein the aliphatic polyether polyurethane polymer is impregnated with or coated with a fatty acid.

6. The medical device of claim 5, wherein the fatty acid is caprylic acid (octanoic acid), caproic acid, lauric acid, or decanoic acid.

7. The medical device of claim 1, wherein the aliphatic polyether polyurethane polymer has a repeating unit of the formula: $[-O(CH_2)_n]_m-OC(O)NH-(CH_2)_x-NHC(O)-$; wherein n=1-4, x=1-12, m is 1-100; wherein the repeating unit repeats 1-250 times, and the terminus of the polymer is hydrogen.

8. The medical device of claim 7, wherein x=1-10.

9. The medical device of claim 1, wherein the second antimicrobial polymer layer further comprises a polyurethane, a silicone, a vinyl, a fluoropolymer, an olefin, or a polymer blend or copolymer thereof.

10. The medical device of claim 9, wherein the second antimicrobial polymer layer is a polyurethane coating.

11. The medical device of claim 10, wherein the polyurethane coating is an aliphatic polyether polyurethane.

12. The medical device of claim 10, wherein the polyurethane coating has a durometer of A or D, or the polyurethane coating comprises a blend of A and D durometer aliphatic polyether polyurethanes.

13. The medical device of claim 1, wherein the second antimicrobial polymer layer comprises a blend of A and D durometer aliphatic polyether polyurethanes.

14. The medical device of claim 1, wherein the medical device does not comprise a penetrating or alkalizing agent.

15. The medical device of claim 1, wherein the catheter is a vascular catheter, a urinary catheter, an intracranial catheter, an intraspinal catheter, a peritoneal catheter, a central nervous system catheter, a cardiovascular catheter, a drainage catheter, a soaker catheter, an aspirating catheter, an intrathecal catheter, a neural catheter, a stimulating catheter, or an epidural catheter.

16. The medical device of claim 15, wherein the catheter is a vascular catheter.

17. The medical device of claim 16, wherein the vascular catheter is a central venous catheter, an arterial line, a pulmonary artery catheter, a peripheral venous catheter, an intravenous catheter, or an intraarterial catheter.

18. The medical device of claim 17, wherein the medical device does not comprise a penetrating or alkalizing agent.

19. The medical device of claim 1, wherein the minocycline and rifampin have been impregnated in the aliphatic polyether polyurethane polymer, and wherein the polymer coating solution does not comprise a penetrating or alkalizing agent.

20. The medical device of claim 1, wherein the aliphatic polyether polyurethane polymer further comprises an additional therapeutic agent.

21. The medical device of claim 20, wherein the additional therapeutic agent is impregnated in the aliphatic polyether polyurethane.

22. The medical device of claim 20, wherein the therapeutic agent is an antimicrobial agent or an antithrombogenic.

23. The medical device of claim 1, wherein at least a portion of the medical device is further coated with a hydrogel polyetherurethane.

24. The medical device of claim 23, wherein the hydrogel polyetherurethane is a polyurethane copolymer.

25. The medical device of claim 1, wherein a surface of the medical device is coated or impregnated with a chelator.

26. The medical device of claim 1, wherein the catheter is a drainage catheter or a vascular catheter.

27. A medical device, comprising a polymer solvent impregnated with minocycline and rifampin, wherein the polymer has not been solvent impregnated with chlorhexidine, gendine, or gardine, and wherein a surface of the polymer is coated with a polyurethane polymer coating, wherein the polyurethane polymer coating comprises (i) a fatty acid or a guanidium compound and (ii) chlorhexidine; wherein the medical device is a catheter.

28. An antimicrobial catheter, wherein a body of the catheter comprises an A durometer aliphatic polyether polyurethane polymer, wherein the aliphatic polyether polyurethane polymer is solvent impregnated either with
    (i) minocycline and rifampin; or
    (ii) chlorhexidine, gendine, or gardine;
        wherein the body of the catheter is coated with an aliphatic polyether polyurethane polymer comprising chlorhexidine, gendine, or gardine.

29. The antimicrobial catheter of claim 28, wherein the aliphatic polyether polyurethane polymer coating comprises gendine.

30. A method of catheterization comprising inserting a catheter of claim 28 or claim 1 into a subject.

31. A catheter comprising:
    a polymer tubing comprising an aliphatic polyether polyurethane polymer coating on the polymer tubing,
    wherein the polymer tubing is an aliphatic polyether polyurethane polymer or a polyurethane polymer;
    wherein the polymer tubing is solvent impregnated with minocycline and rifampin, and wherein the polymer tubing has not been solvent impregnated with chlorhexidine, gendine, or gardine; and
    wherein the aliphatic polyether polyurethane polymer coating comprises chlorhexidine, gendine, or gardine.

32. An antimicrobial catheter, wherein a body of the catheter comprises an A durometer aliphatic polyether polyurethane polymer,
    wherein the aliphatic polyether polyurethane polymer is solvent impregnated with chlorhexidine, gendine, or gardine; and wherein the aliphatic polyether polyurethane polymer has not been solvent impregnated with minocycline or rifampin;
    and wherein the body of the catheter is coated with an aliphatic polyether polyurethane polymer comprising minocycline and rifampin.

* * * * *